US010925468B2

(12) United States Patent
Tseng

(10) Patent No.: US 10,925,468 B2
(45) Date of Patent: Feb. 23, 2021

(54) COLONOSCOPE

(71) Applicant: Chin-Shun Tseng, Kaohsiung (TW)

(72) Inventor: Chin-Shun Tseng, Kaohsiung (TW)

( * ) Notice: Subject to any disclaimer, the term of this patent is extended or adjusted under 35 U.S.C. 154(b) by 0 days.

(21) Appl. No.: 16/208,631

(22) Filed: Dec. 4, 2018

(65) Prior Publication Data

US 2019/0099067 A1 Apr. 4, 2019

Related U.S. Application Data

(63) Continuation-in-part of application No. 15/208,683, filed on Jul. 13, 2016, now abandoned.

(30) Foreign Application Priority Data

Jul. 16, 2015 (TW) .............................. 104123100 A

(51) Int. Cl.
*A61B 1/00* (2006.01)
*A61B 5/06* (2006.01)
(Continued)

(52) U.S. Cl.
CPC ...... *A61B 1/00156* (2013.01); *A61B 1/00006* (2013.01); *A61B 1/00029* (2013.01); *A61B 1/00032* (2013.01); *A61B 1/00071* (2013.01); *A61B 1/00114* (2013.01); *A61B 1/00119* (2013.01); *A61B 1/00158* (2013.01); *A61B 1/00181* (2013.01); *A61B 1/015* (2013.01); *A61B 1/018* (2013.01); *A61B 1/041* (2013.01); *A61B 1/045* (2013.01); *A61B 1/051* (2013.01); *A61B 1/0607* (2013.01); *A61B 1/0661* (2013.01); *A61B 1/0676* (2013.01); *A61B 1/0684* (2013.01); *A61B 1/31* (2013.01); *A61B 5/062* (2013.01); *A61B 5/067* (2013.01)

(58) Field of Classification Search
CPC ...... A61B 1/00091; A61B 1/015; A61B 1/041
See application file for complete search history.

(56) References Cited

U.S. PATENT DOCUMENTS 5,353,807 A   10/1994  DeMarco
5,984,860 A * 11/1999  Shan .................. A61B 1/041
                                              600/110
(Continued)

FOREIGN PATENT DOCUMENTS

EP    0792130 B1    7/2000
TW    201400074 A   1/2014

*Primary Examiner* — Aaron B Fairchild
(74) *Attorney, Agent, or Firm* — Alan D. Kamrath; Karin L. Williams; Mayer & Williams PC

(57) ABSTRACT

A colonoscope including an egg-shaped image-capturing module and a wiring unit is disclosed. The image-capturing module includes a casing, a first image detector, a vibration motor and a control unit. The casing has first and second ends. The first end is made of a transparent material. The first image detector captures a first image. The vibration motor is configured to vibrate the casing. The control unit controls the first image detector to capture the first image. The control unit controls the vibration of the vibration motor. The wiring unit includes a vent and includes a plurality of lead wires and an air tube. Power can be transmitted to the control unit through the plurality of lead wires. The air tube is configured to convey air, and the vent is configured to output the air to a colon.

11 Claims, 23 Drawing Sheets

(51) Int. Cl.
*A61B 1/045* (2006.01)
*A61B 1/015* (2006.01)
*A61B 1/05* (2006.01)
*A61B 1/018* (2006.01)
*A61B 1/04* (2006.01)
*A61B 1/31* (2006.01)
*A61B 1/06* (2006.01)

(56) References Cited

U.S. PATENT DOCUMENTS

| | | |
|---|---|---|
| 2004/0050394 A1 | 3/2004 | Jin |
| 2005/0187479 A1 | 8/2005 | Graumann |
| 2007/0118017 A1 | 5/2007 | Honda |
| 2009/0264701 A1 | 10/2009 | Ito |
| 2009/0306475 A1 | 12/2009 | Yamamoto et al. |
| 2010/0081876 A1 | 4/2010 | Linenkugel et al. |
| 2013/0345506 A1 | 12/2013 | Lien et al. |
| 2014/0350341 A1 | 11/2014 | Slattery, Jr. et al. |

* cited by examiner

COLONOSCOPE

CROSS REFERENCE TO RELATED APPLICATIONS

The application claims the benefit of Taiwan application serial No. 104123100, filed on Jul. 16, 2015, and the entire contents of which are incorporated herein by reference.

This is a continuation-in-part application of U.S. patent application Ser. No. 15/208,683 filed on Jul. 13, 2016.

BACKGROUND OF THE INVENTION

1. Field of the Invention

The present invention generally relates to a colonoscope and, more particularly, to a colonoscope including an egg-shaped image-capturing module.

2. Description of the Related Art

In Taiwan, cancers have been the leading cause of death for 33 consecutive years. Among various cancers, colon cancer and rectal cancer have remained the top three causes of death. In 2014, there were up to 15,000 people who were diagnosed with cancers, which resulted in a death toll of 5,000. In Japan, there are 45,000 people who are diagnosed with cancers every year, which resulted in a death toll of 18,000. In America, there are approximately 150,000 people diagnosed with cancers every year, which leads to a death toll of approximately 50,000. The cancers are highly related to colon polyps. In Taiwan, there are approximately 710,000 people who have colon polyps among adults aged 20-49 years. The colon polyps can lead to colon cancer in 5-10 years. Thus, if colon polyps are properly handled, colon cancer can be prevented in most cases.

Currently, a colonoscope is the medical instrument that is used to examine colon polyps. The main manufacturer of the colonoscope is Olympus Medical Systems Corp, whose colonoscopes are constructed by fibers. However, the use of the fiber material makes it difficult to bend the tube when it is needed to adjust the position of the lens. Second, the colonoscope has a length of approximately 180 cm. Therefore, if it is needed to examine the entire colon in a full length, general anesthetics is required. However, since anesthetics have some risk, most patients are not willing to accept general anesthetics. In addition, pumping the air into the intestinal tract during the examination will cause abdominal distension, and the insertion and propelling of the thick, long tube in the colon will exert a pressing force on the intestinal wall of the colon. Therefore, most of the patients suffer a great pain during the examination, and even have a hard time finishing the colonoscopy. Furthermore, several domestic researches revealed that there is about 0.25% to 0.5% chance that the intestinal perforation can be resulted during the colonoscopy due to some factors such as improper operation of the colonoscope, the special condition of the patient, or the hot biopsy of the polyps. This often leads to a medical litigation. Thus, the colonoscopy has a lot of risks by itself. In the position of the patients, they are concerned about the risk of intestinal perforation. In the position of the doctors, they are concerned about the risk of medical litigation. Due to the reasons, colonoscopy is not widely accepted, and many people do not know they have colon polyps since they are not willing to accept the colonoscopy. This leads to a higher chance of colon cancer.

In light of the deficiency where it is difficult to bend the tube to adjust the propelling direction of the tip of the tube, some aids have been proposed to straighten the colon such as an external straighter as disclosed in European Patent No. 0792130B1. Such an aid has a protuberance. Due to this, the aid can press the colon and therefore straighten the colon. Then, the tube can be inserted deep into the colon. A similar aid was also proposed by U.S. Patent No. 2014/0350341A1. However, these aids are no longer helpful at the sharp bend of the intestinal tract, such as at the location where the descending colon connects to the transverse colon, as well as the location where the transverse colon connects to the ascending colon.

In addition to straightening the colon through the use of the aids, a bendable colonoscope was also proposed (by changing the structure of the colonoscope) to overcome the difficulty in bending the tube of the conventional colonoscope. For example, Taiwan Patent No. I468140 discloses a magnetically-controlled system applicable for colonoscopy. Such a system includes an external magnetic member and an internal magnetic member. The internal magnetic member is mounted on a bar-shaped instrument of the colonoscope, and the external magnetic member is mounted on an external device. Based on this, the external magnetic member can guide the internal magnetic member to change its propelling direction. As such, the bar-shaped instrument is able to change its propelling direction at the bends of the colon. Although this type of colonoscope overcomes the difficulty in bending the tube of the conventional colonoscope, its bar-shaped instrument is still as thick as the tube of the conventional colonoscope. Although the bar-shaped instrument of the colonoscope can change its propelling direction in the colon, it tends to exert a pressing force on the intestinal wall of the colon if a slight mistake is made (due to poor skill or oversight) during the propelling of the bar-shaped instrument, resulting in a hard contact between the bar-shaped instrument and the intestinal wall of the colon. As a result, the patient still suffers a great pain during the examination.

Besides, for any type of the conventional colonoscope (including the one disclosed in Taiwan Patent No. I468140), there exists some blind spots around the folds of the colon where the viewing thereof is hardly possible. In other words, the conventional colonoscope has only one direction of view. Disadvantageously, the colonoscope is not able to view the back side of the fold, leading to an incomplete examination.

Therefore, a colonoscope that provides a nearly pain-free examination will certainly be advantageous in preventing the colon cancer. Thus, it has been an important issue among the manufacturers of the medical instrument to develop a colonoscope which is easy to operate, has no blind spot, provides a nearly pain-free examination, and meets various demands of the doctors.

SUMMARY OF THE INVENTION

It is therefore an objective of the invention to provide an egg-shaped image-capturing module of a colonoscope, in which the colonoscope has a highly flexible tube, is easy to operate, and provides a nearly pain-free colonoscopy.

In an embodiment of the invention, a colonoscope having an egg-shaped image-capturing module, a wiring unit and a power supply member is disclosed. The image-capturing module includes a casing, a first image detector, a vibration motor and a control unit. The casing has a first end and a second end. The first and second ends are spaced from each other in an axial direction thereof. The first end is made of a transparent material. The first image detector is arranged at the first end of the casing to provide an illumination effect and to capture a first image in a first direction. The vibration motor is arranged in the casing to vibrate the casing. The control unit is electrically connected to the first image detector and the vibration motor. The control unit controls the first image detector to capture the first image and controls the transmission of the captured first image upon the reception of a command. The control unit controls the vibration of the vibration motor. The wiring unit is fixed to the second end of the casing and includes an outer sheath and an air tube. The air tube is made of a flexible material and is enveloped in the outer sheath. The wiring unit includes a power supply member electrically connected to the control unit. The power supply member provides power to the first image detector and the vibration motor. The casing or the wiring unit includes a vent that is in communication with the air tube of the wiring unit. The air tube is configured to convey air, and the vent is configured to output the air to a colon.

In an example, the colonoscope further includes a second image detector arranged at the second end of the casing, and the second image detector is configured to capture a second image in a second direction substantially opposite to the first direction.

In the example, the colonoscope further includes an angle detection unit electrically connected to the control unit. The angle detection unit is configured to detect an inclined angle of the casing with respect to a horizontal line. The control unit transmits a detected result of the inclined angle to a display.

In the example, the angle detection unit is a microelectromechanical angle detection chip, a microelectromechanical gyroscope chip, a microelectromechanical dual-axis acceleration detection chip, a microelectromechanical tri-axis acceleration detection chip, a rolling switch or a magnetic sensor.

In the example, the colonoscope further includes at least one propelling auxiliary arranged on an outer surface of the casing and configured to facilitate propelling the image-capturing module.

In the example, the power supply member is in a form of a plurality of lead wires contained in the wiring unit.

In the example, the colonoscope further includes a power-line signal transmission module or the wiring unit further includes a signal line. The power-line signal transmission module is electrically connected to the control unit. The power-line signal transmission module and the signal line are configured to transmit the captured first image to a display.

In the example, the casing has a length of 2.5-5.2 cm and a width of 1.5-2.5 cm.

In the example, the wiring unit or the air tube further includes an instrument channel provided for insertion of an instrument. The instrument channel has an outlet at the first end of the casing. The instrument is configured to extend into the instrument channel and extend out of the outlet for performing a surgery.

In the example, the colonoscope further includes a telescopic propelling control unit connected between the first end and the second end of the casing, and the casing has a lateral wall made of a flexible material.

In the example, the casing includes at least one propelling auxiliary on an outer surface thereof.

In the example, the telescopic propelling control unit includes a drive motor, a telescopically driving member and a telescopically driven member. The drive motor is mounted to an inner side of the lateral wall. The telescopically driving member is rotatably coupled with the drive motor. The telescopically driven member is mounted to at least one of the first and second ends.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1A:
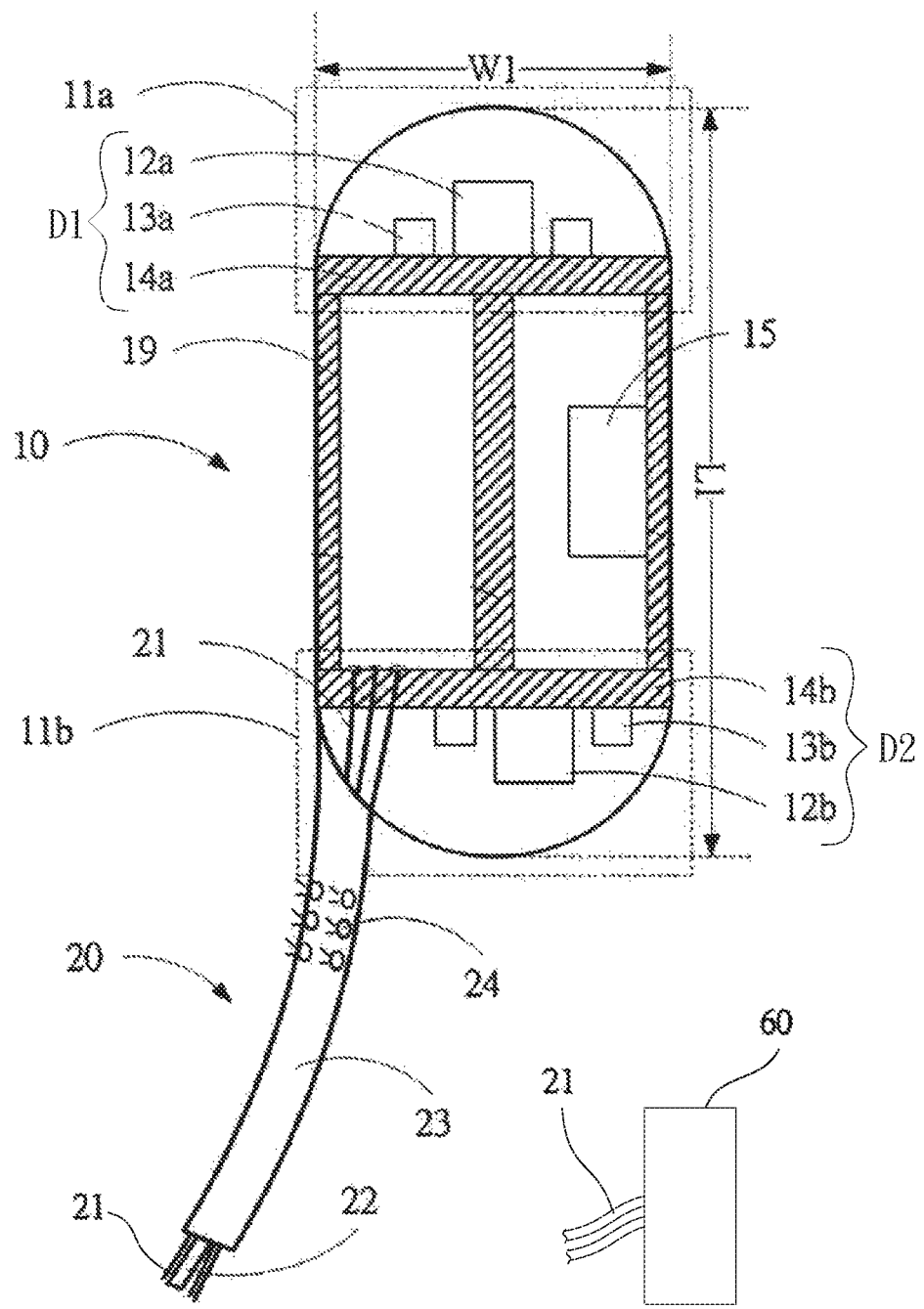
FIG. 1A is a cross sectional view of an egg-shaped image-capturing module of a colonoscope according to a first embodiment of the invention.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

In an embodiment of the invention, a colonoscope having an egg-shaped image-capturing module and a propelling method of the image-capturing module are disclosed. The image-capturing module can be smoothly contained in the intestinal tract of a patient due to its egg shape. Then, the image-capturing module can propel along the intestinal tract under a vibration force. Although the image-capturing module needs to change its propelling direction at the bends of the intestinal tract, it will not cause uncomfortable feeling of the patient. The image-capturing module is also connected with a flexible wiring unit which provides the required power to the image-capturing module. Air (or gas) can also be pumped into the intestinal tract to properly expand the intestinal tract under the operation of the doctor, allowing the doctor to examine the condition of the colon. The detailed structure and function of the image-capturing module is discussed below.

FIG. 1A is a cross sectional view of an egg-shaped image-capturing module of a colonoscope according to a first embodiment of the invention. The image-capturing module includes an egg-shaped casing 10, a wiring unit 20 and a control unit 60. The egg-shaped casing 10 includes a first image-capturing unit, a second image-capturing unit and a vibration motor 15. The egg-shaped casing 10 has a first end 11a, a second end 11b and a central cylinder. The first end 11a and the second end 11b are opposite to each other in an axial direction of the image-capturing module. The central cylinder extends in the axial direction of the image-capturing module. Both the first end 11a and the second end 11b are made of transparent material. The first image detector D1 is arranged at the first end 11a and includes a first image capturing device 12a, a first light emitting unit 13a and a first circuit board 14a. The second image detector D2 is arranged at the second end 11b and includes a second image capturing device 12b, a second light emitting module 13b and a second circuit board 14a. The first and second image detectors D1 and D2 are used to provide an illumination effect and capture the images (such as video image). The first image detector D1 is used to capture the image in a first direction, and the second image detector D2 is used to capture the image in a second direction substantially opposite to the first direction. When the first image detector D1 captures the image in the first direction, there are always some blind spots around the folds of the colon which are hidden from the first image detector D1. In light of this deficiency, the second image detector D2 is used to capture the images of the blind spots of the first image detector D1. The vibration motor 15 is arranged in the egg-shaped casing 10 and provides a vibration force for the casing 10. The control unit 60 is arranged outside the egg-shaped casing 10.

Figure 1B:
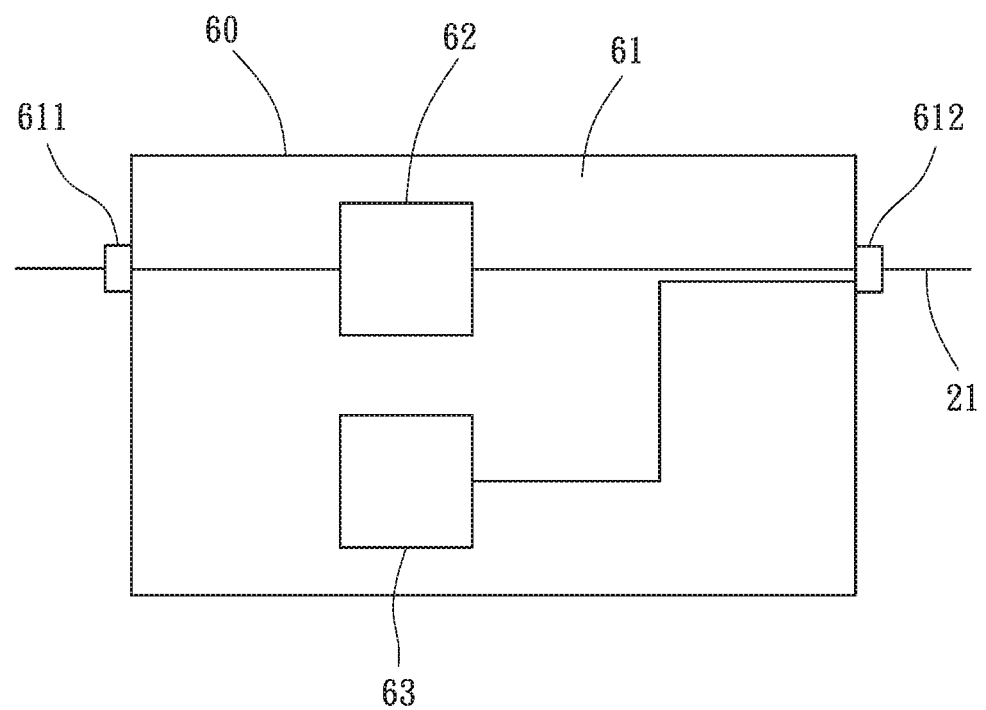
FIG. 1B shows a block diagram of a control unit of the egg-shaped image-capturing module of the colonoscope according to the first embodiment of the invention.

FIG. 1B shows a block diagram of the control unit 60. The control unit 60 includes a circuit board 61 having an input port 611 and an output port 612. The input port 611 is connected to a power cable (shown but not labeled) to receive the power required for its operation. The wiring unit 20 includes a plurality of lead wires 21 connected to the output port 612. A vibration controller 62 and an illuminance adjustor 63 are mounted on the circuit board 61 and are connected to the output port 612. The plurality of lead wires 21 serves as a power supply member electrically connected to the control unit 60. The plurality of lead wires 21 may include three lead wires 21, namely, a positive power line, a negative power line and a signal line. Electricity can be supplied to the elements in the casing 10 (such as the first and second image detectors D1 and D2 and the vibration motor 15) through the positive and negative power lines. The vibration controller 62 is configured to vibrate the vibration motor 15. The vibration controller 62 may be a switch (but is not limited thereto). When the switch is connected, the vibration motor 15 vibrates and vice versa. The illuminance adjustor 63 is configured to adjust the light intensity of the first and second image detectors D1 and D2. The illuminance adjustor 63 may be a rheostat but is not limited thereto.

In the above arrangement, upon the reception of an external command, the control unit 60 controls the first and second image detectors D1 and D2 to capture the images and transmits the captured images to a display via the signal line. Thus, the doctor can view the image of the intestinal tract through the display. The wiring unit 20 is fixed to the second end 11b of the casing 10 and further includes an air tube 22. The plurality of lead wires 21 and the air tube 22 are enveloped in an outer sheath 23. In this embodiment, the outer sheath 23 includes a plurality of vents 24. The pumped air is sent into the colon via the plurality of vents 24.

Figure 1C:
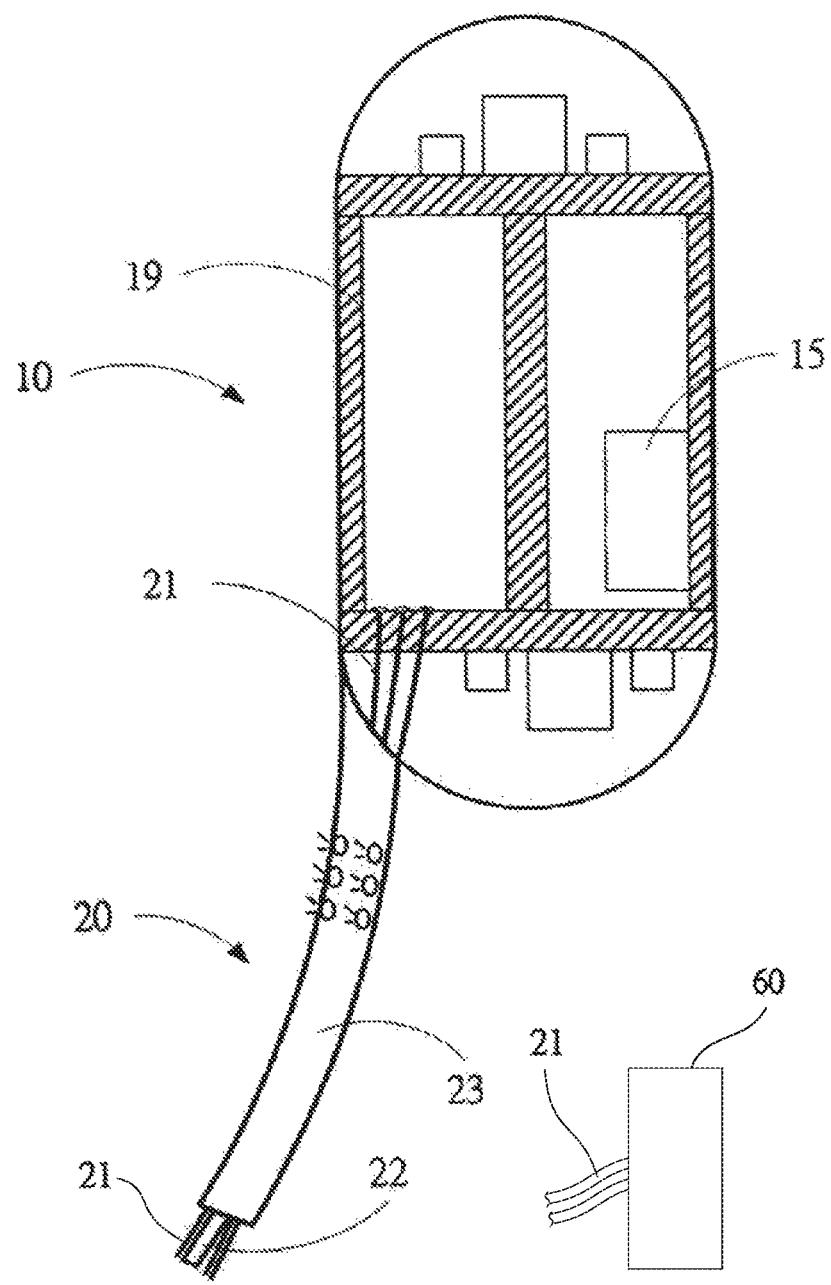
FIG. 1C is a cross sectional view of the egg-shaped image-capturing module of the colonoscope of the first embodiment where the vibration motor is mounted to a different position of the central cylinder of the casing.

In the first embodiment, the vibration motor 15 is mounted to an inner wall 19 of the casing 10. Namely, the vibration motor 15 is mounted to an inner wall of the central cylinder of the casing 10. As shown in FIG. 1A, the vibration motor 15 is mounted to a central position of the central cylinder of the casing 10. However, the vibration motor 15 can also be mounted to a lower position of the central cylinder of the casing 10 which is adjacent to the second end 11b as shown in FIG. 1C, or is mounted to an upper position of the central cylinder of the casing 10 which is adjacent to the first end 11a. In the cases of the lower and upper positions, the upper position is preferred.

Both the first and second image capturing devices 12a and 12b include a high-resolution CMOS or CCD sensor. Both the first and second light emitting units 13a and 13b include a light-emitting module formed by light-emitting diodes (LED). The casing 10 has a length L1 between 2.5 and 5.2 cm and a width W1 between 1.5 and 2.5 cm.

Figure 2:
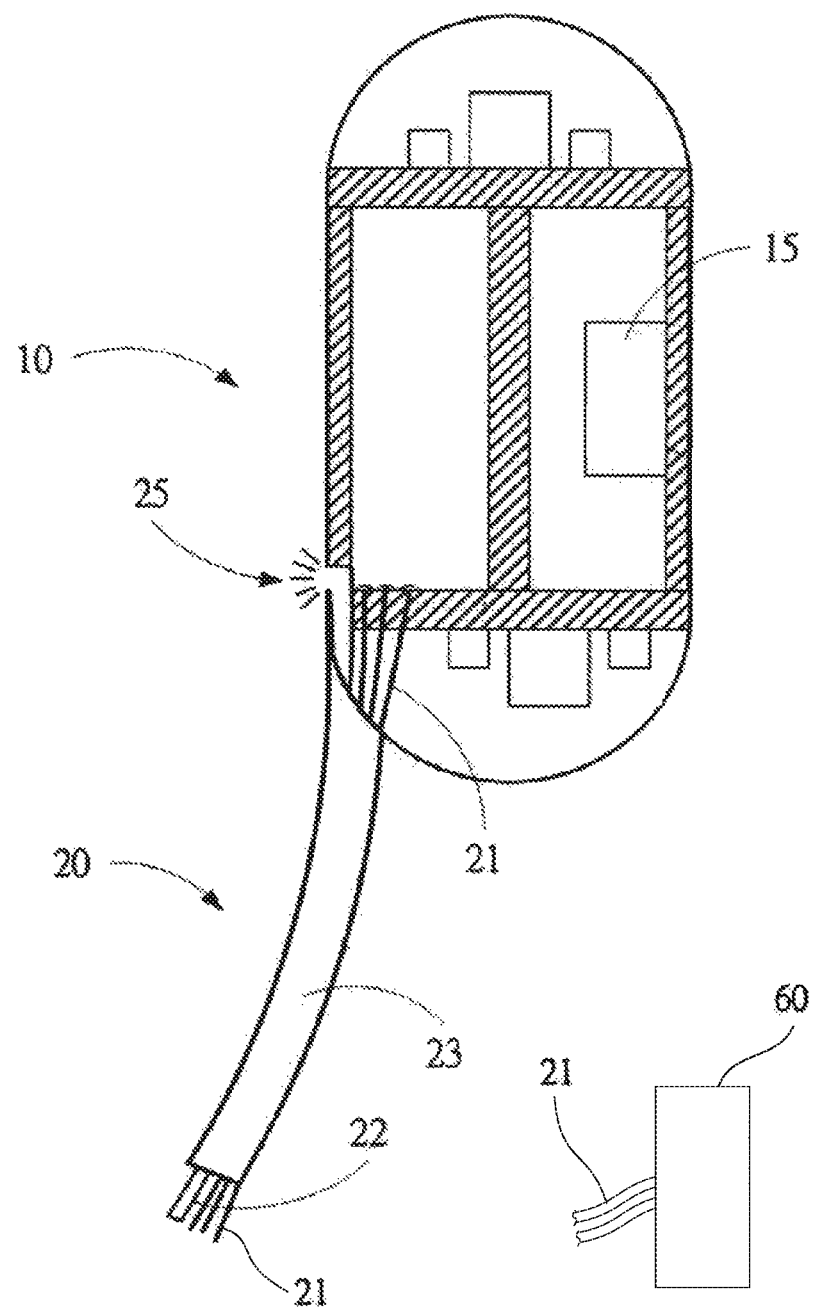
FIG. 2 is a cross sectional view of the egg-shaped image-capturing module of the colonoscope of the first embodiment where the casing includes a vent.

The action of pumping air into the intestinal tract is an external operation, but this is the main function that the colonoscope needs to provide. Although a plurality of vents 24 can be formed on the wiring unit 20 at a location adjacent to the second end 11b of the casing 10 as shown in FIG. 1A, the casing 10 may also include a vent 25 in replacement of the plurality of vents 24 as shown in FIG. 2.

Although the air can be pumped into the intestinal tract via the vent 25, water or medicinal liquid can also be pumped into the intestinal tract according to the requirement.

Figure 3A:
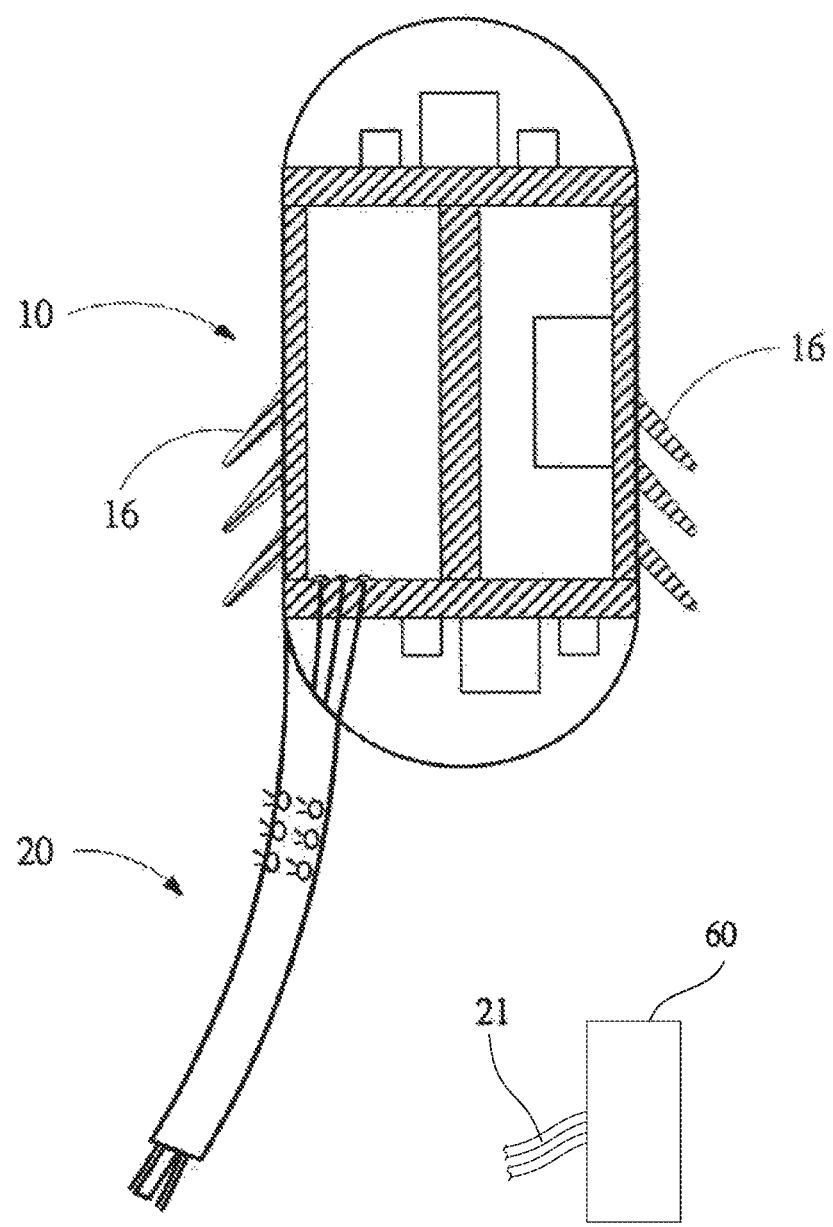
FIG. 3A is a cross sectional view of the egg-shaped image-capturing module of the colonoscope of the first embodiment where the casing is provided with a plurality of propelling auxiliaries.
Figure 3B:
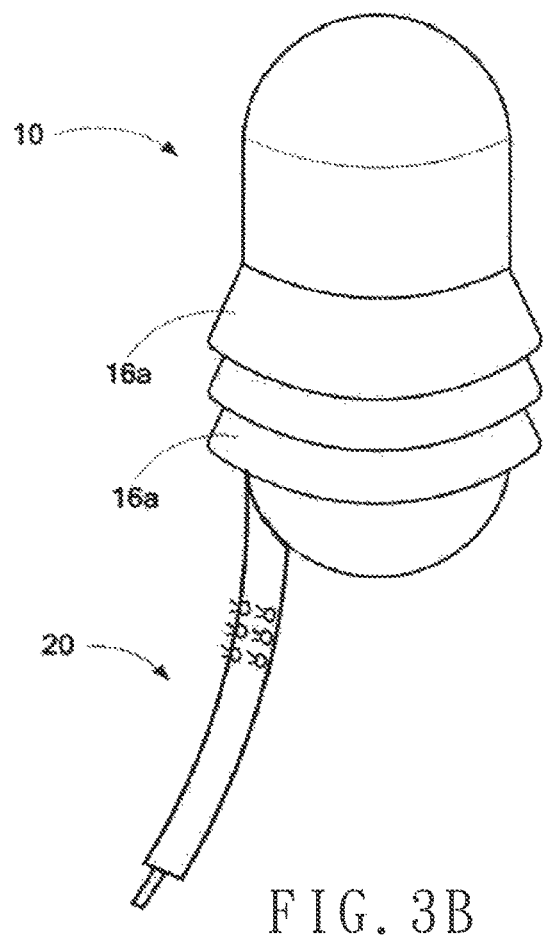
FIG. 3B shows the egg-shaped image-capturing module of FIG. 3A where each of the plurality of propelling auxiliaries is in an annular form.
Figure 3C:
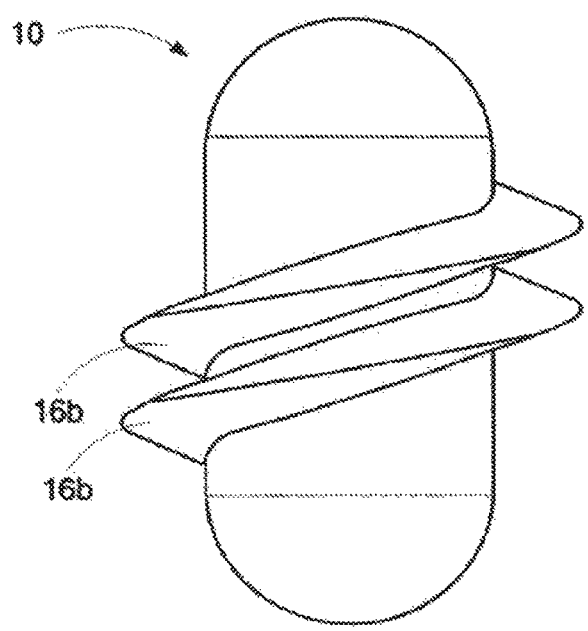
FIG. 3C shows the egg-shaped image-capturing module of FIG. 3A where each of the plurality of propelling auxiliaries is in a helical form.

To facilitate propelling the image-capturing module, the casing 10 of the image-capturing module can be provided with at least one propelling auxiliary 16 (each may be in the form of a protrusion formed on the casing 10). As shown in FIGS. 3A, 3B and 3C, the at least one propelling auxiliary 16 includes a first propelling auxiliary 16a and a second propelling auxiliary 16b. The arrangement of the first and second propelling auxiliaries 16a and 16b ensures a smooth propelling of the casing 10 in the colon. Each of the first and second propelling auxiliaries 16a and 16b may be in an annular form (as shown in FIG. 3B), a helical form (as shown in FIG. 3C) or in the shape of snake's scales, or any combination thereof.

Figure 4A:
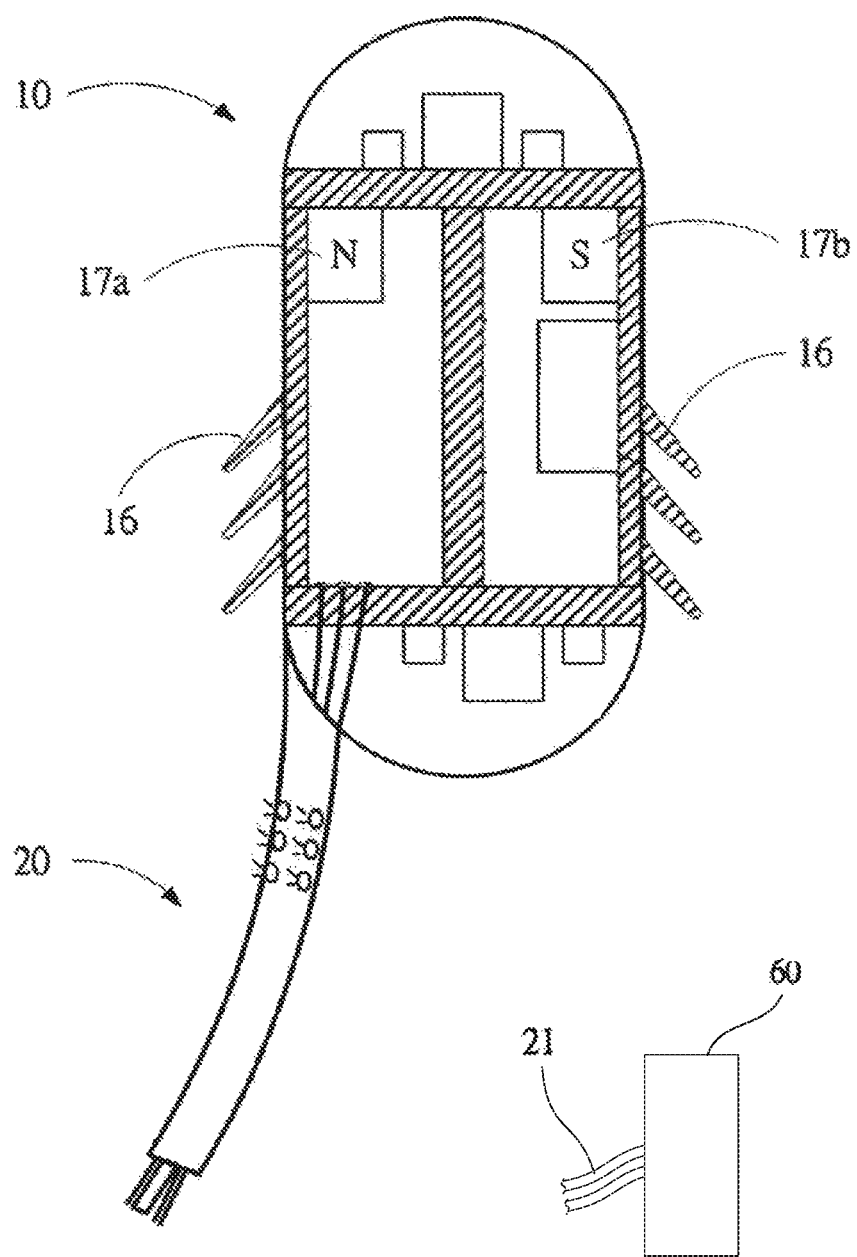
FIG. 4A is a cross sectional view of the egg-shaped image-capturing module of the first embodiment, in which the image-capturing module is provided with the at least one internal magnetic member.
Figure 4B:
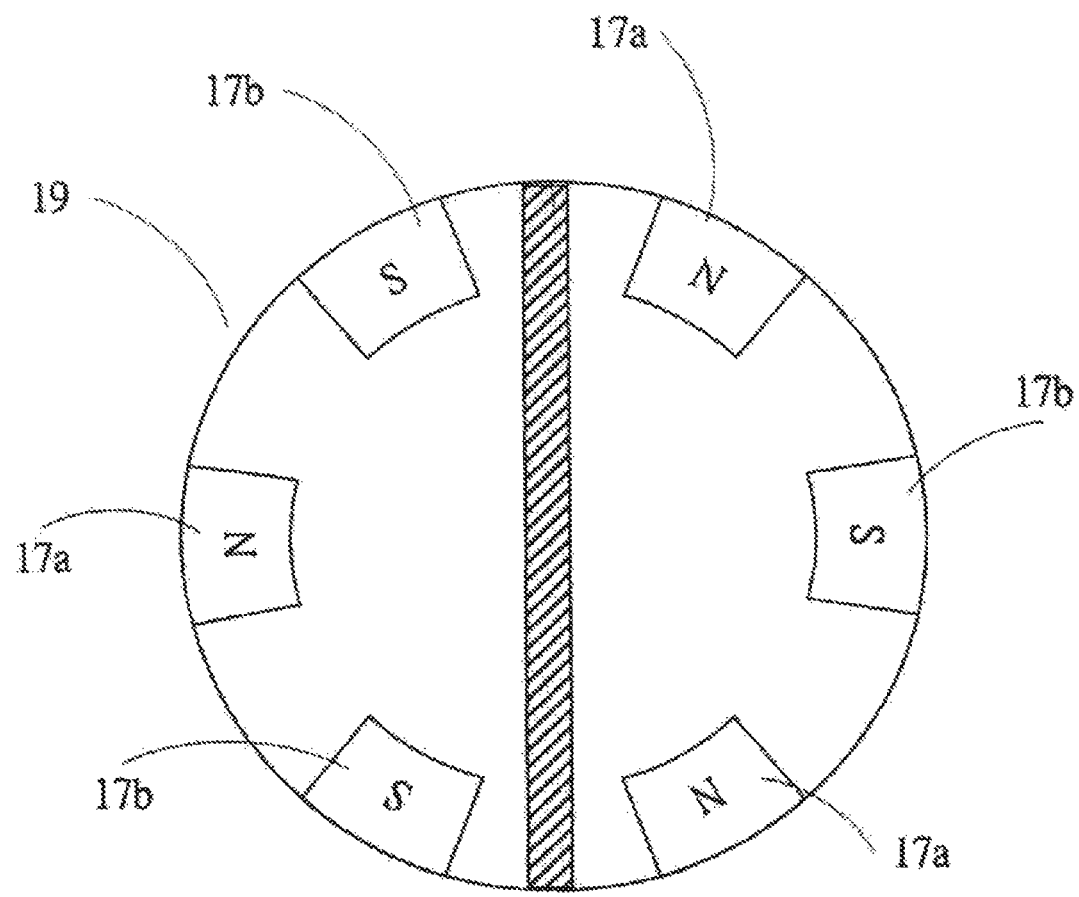
FIG. 4B is a radially cross sectional view of the image-capturing module of FIG. 4A.

In addition to the at least one propelling auxiliary 16, the egg-shaped image-capturing module also includes at least one internal magnetic member according to a second modification of the first embodiment of the invention. FIG. 4A is a cross sectional view of the egg-shaped image-capturing module that is provided with the at least one internal magnetic member, and FIG. 4B is a top view of the image-capturing module. In the second modification of the first embodiment of the invention, three internal magnetic members are arranged on the central cylinder at a position adjacent to the first end 11a. Each of the internal magnetic members includes an N-pole element 17a and an S-pole element 17b. Based on this, an external magnetic member that is magnetically attracted to the internal magnetic member can be provided. The external magnetic member can be used to control the movement and propelling of the casing 10 through the magnetic force between the internal and external magnetic members. Since some parts of the intestinal wall may be hidden from the second image detector D2 due to the obstruction of the wiring unit 20, the casing 10 can be turned by an angle (about a vertical axis) to adjust the viewing angle of the second image detector D2. Specifically, the doctor can place the external magnetic member close to the internal magnetic member. When the external and internal magnetic members are close enough to each other, they will be magnetically attracted to each other by the magnetic force. In this regard, when the doctor turns the external magnetic member at an angle, the internal magnetic member also turns by the angle. As a result, the casing 10 is turned and the viewing direction of the second image detector D2 is changed. In another case, the doctor can simply propel the external magnetic member without turning the external magnetic member. In this situation, the propelling of the external magnetic member will bring the internal magnetic member to move forward, thus facilitating the propelling of the casing 10. Furthermore, the precise location of the casing 10 in the intestinal tract can be detected through the magnetic field generated by the internal magnetic member, allowing the doctor to precisely indicate the location of the affected part.

Figure 5:
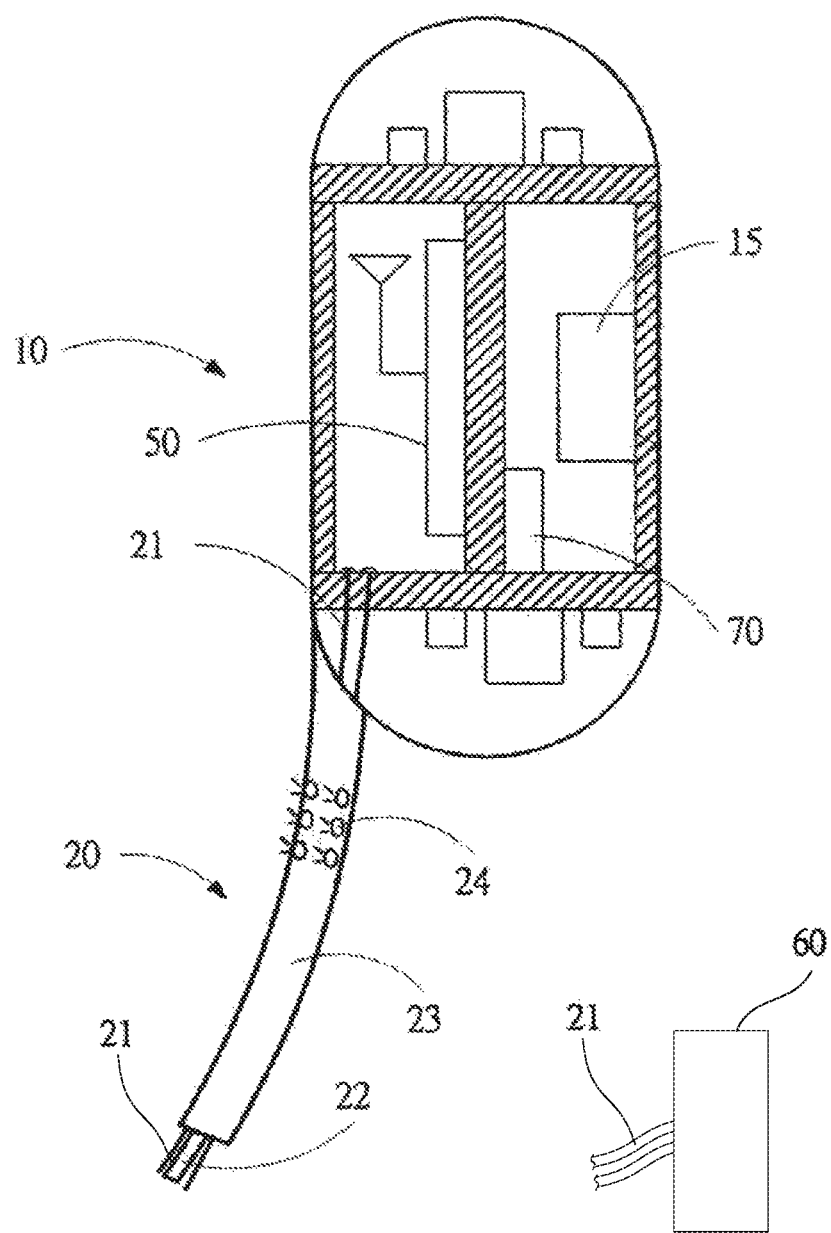
FIG. 5 is a cross sectional view of the egg-shaped image-capturing module including a wireless transmission module.

Moreover, due to the arrangement of the wiring unit 20, there will be a sufficient amount of power for image transmission. The image can be transmitted to the display in a wired or wireless manner. In the wired transmission, signals can be transmitted over the signal line or the power line. Alternatively, the casing 10 may be further provided with a power-line signal transmission module. The control unit 60 can transmit the instant images of the first and second image detectors D1 and D2 to the display in either case (through the signal line or the power-line signal transmission module). In case of the power-line signal transmission module, the power line of the wiring unit 20 can be omitted. In addition, FIG. 5 shows a third modification of the first embodiment of the invention. In FIG. 5, a wireless transmission module 50 is provided. The wireless transmission module 50 is electrically connected to the control unit 60 and is used to transmit the images of the first and second image detectors D1 and D2 to the display. The wireless transmission module 50 may operate under the Wi-Fi or Bluetooth technologies or the like.

Besides, in the case of wireless transmission, a battery can be provided in the casing 10 to replace the wiring unit 20. The battery can provide the required power for the casing 10, therefore the positive and negative power lines of the lead wires 21 can be omitted. The wireless transmission module 50 not only transmits the images captured by the first and second image detectors D1 and D2, but also receives and transmits an external command to the control unit 60. Thus, the wiring unit 20 does not need to include some of the plurality of lead wires 21. The wiring unit 20 needs to include only the air tube 22 to perform the function of the egg-shaped image-capturing module of the invention.

FIG. 5 shows a fourth modification of the egg-shaped image-capturing module of the first embodiment of the invention. In the fourth modification, the egg-shaped image-capturing module further includes an angle detection unit 70 electrically connected to the control unit 60. The angle detection unit 70 is used to detect the angle of the casing 10 with respect to the horizontal line. The detected result can be transmitted to the display by the control unit 60. The angle detection unit 70 is used to detect the inclined angle of the egg-shaped image-capturing module when the module propels in the intestinal tract. Namely, the angle detection unit 70 can detect whether the egg-shaped image-capturing module is in an inclined state where the first end 11a of the casing 10 is heading downwards (i.e. the first end 11a of the casing 10 is in a lower level than the second end 11b is). If the egg-shaped image-capturing module is in the inclined state, the image-capturing module can propel in the colon under a vibration force. If the egg-shaped image-capturing module is not in an inclined state (the first end 11a of the casing 10 is in a higher level than the second end 11b or is in the same level as the second end 11b), the doctor can propel the egg-shaped image-capturing module along the intestinal tract using the external magnetic member shown in FIG. 4. In another option, the doctor can adjust the lying posture of the patient to change the inclined angle of the intestinal tract, so as to place the egg-shaped image-capturing module in an inclined state. Therefore, the arrangement of the angle detection unit 70 can facilitate propelling the egg-shaped image-capturing module.

The angle detection unit 70 may be a microelectromechanical angle detection chip, a microelectromechanical gyroscope chip, a microelectromechanical dual-axis acceleration detection chip, a microelectromechanical tri-axis acceleration detection chip, a rolling switch, or a magnetic sensor. Selection of the above elements may be based on the space occupation and vibration resistance. The one with smaller volume and higher vibration resistance is preferred.

Figure 6:
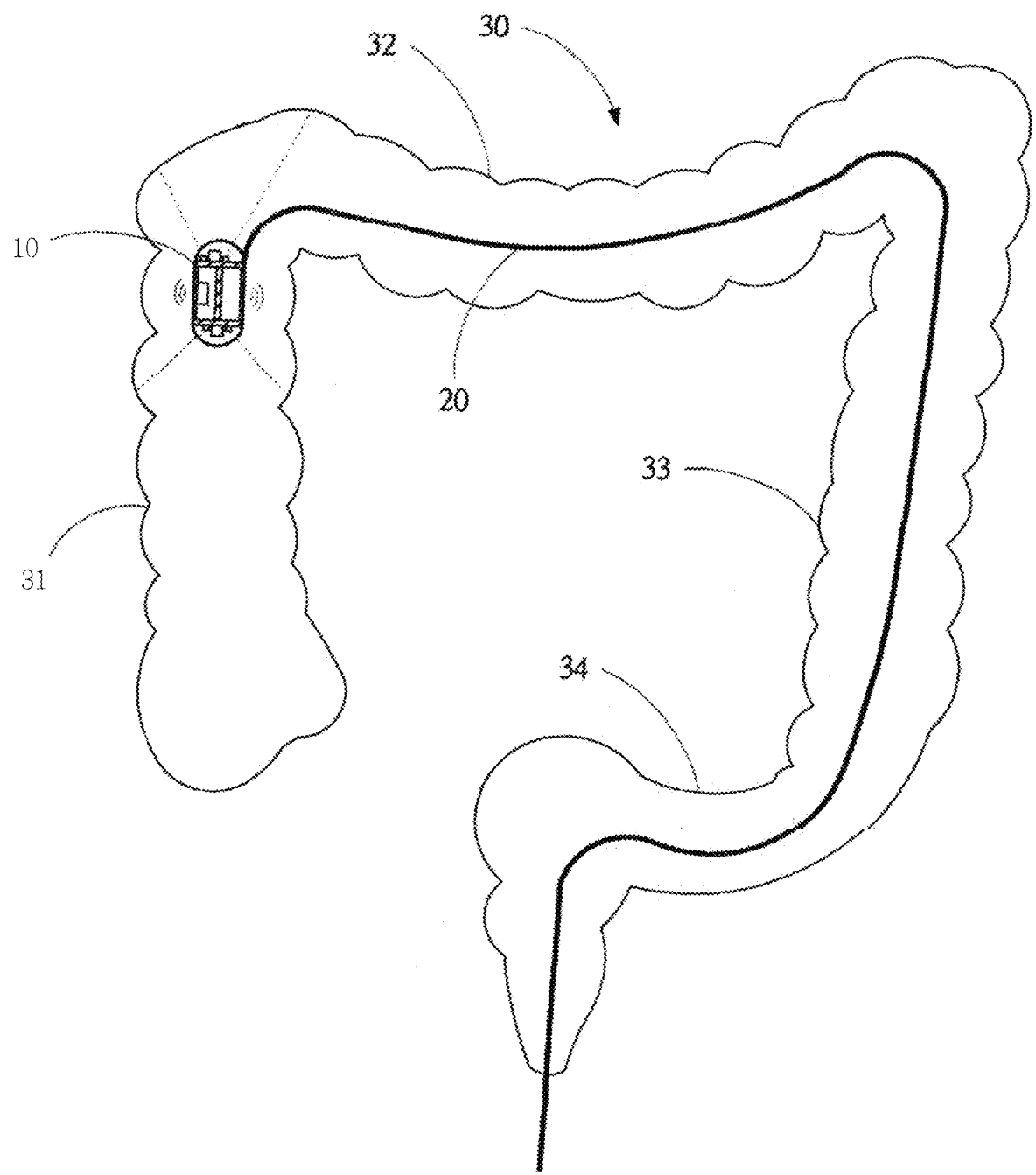
FIG. 6 shows a use of the egg-shaped image-capturing module in a colon according to the first embodiment of the invention.

FIG. 6 shows a use of the egg-shaped image-capturing module in a colon according to the first embodiment of the invention. It can be seen from FIG. 6 that the image-capturing module has an egg shape that fits to the intestinal tract and can be smoothly contained therein. Moreover, since the wiring unit 20 uses an air tube formed by a flexible material, the air tube is flexible and has a diameter smaller than 0.5 cm. Therefore, the wiring unit 20 does not exert a pressing force on the intestinal wall of the colon. As a great advantage, the patient will not feel uncomfortable when the egg-shaped image-capturing module propels in the intestinal tract of the patient. Thus, the egg-shaped image-capturing module can propel through the entire intestinal tract (in a full length of 160 cm, including the rectum 33, the sigmoid 34, the descending colon 33, the transverse colon 32 and the ascending colon 31) in a nearly pain-free manner.

Figure 7A:
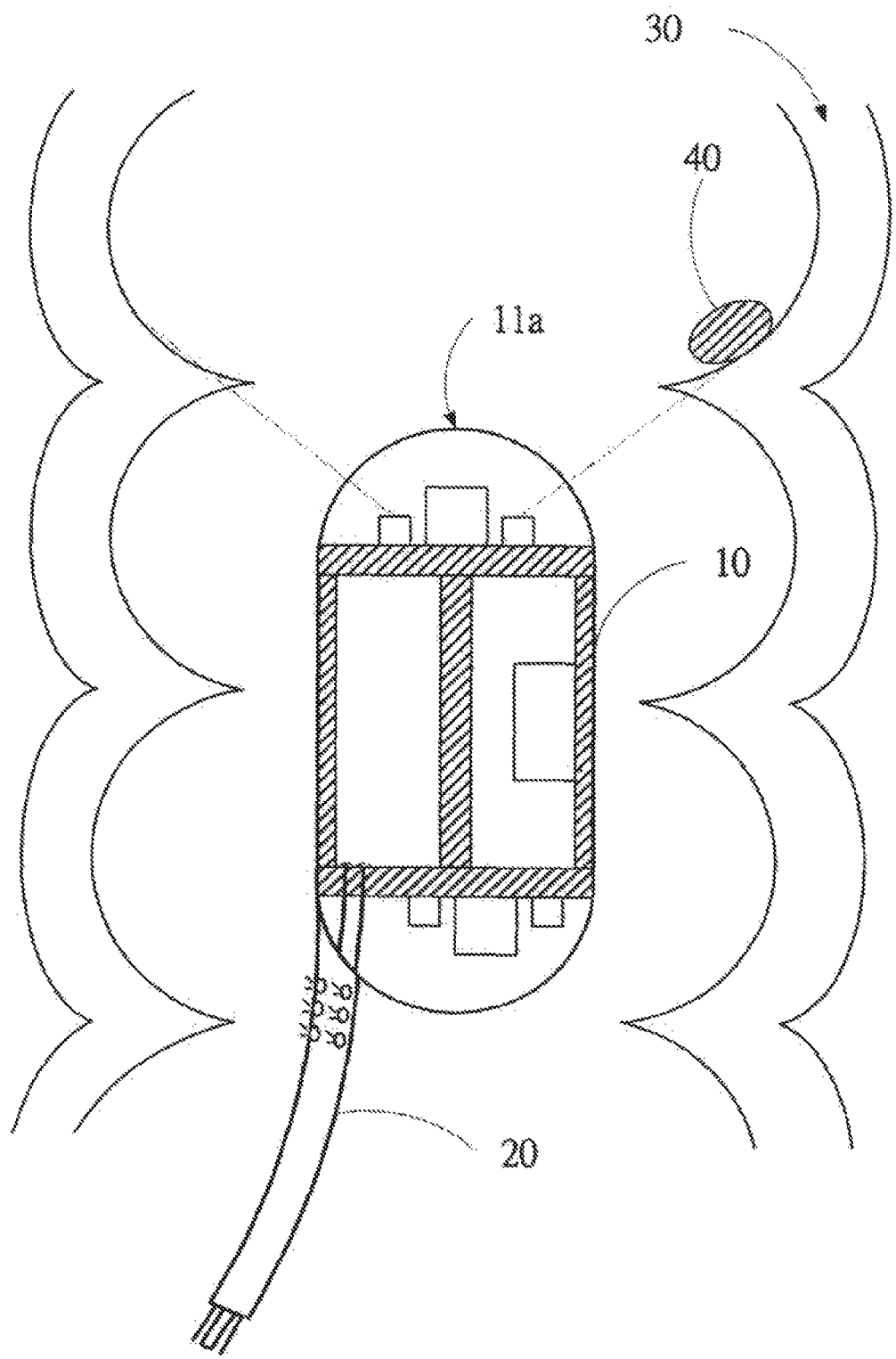
FIG. 7A shows the egg-shaped image-capturing module which is located in a position where a polyp cannot be viewed.
Figure 7B:
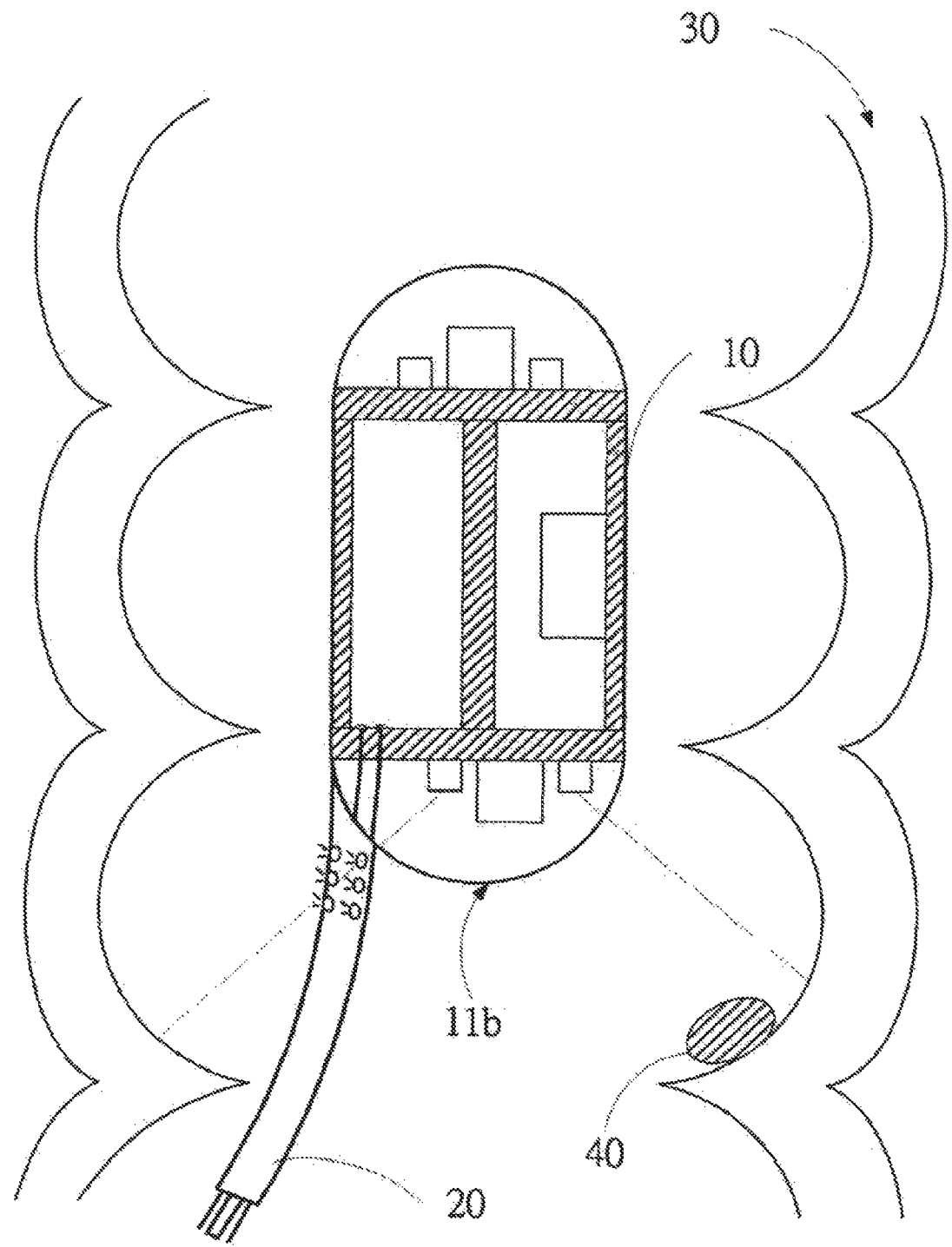
FIG. 7B shows the egg-shaped image-capturing module which moves to another position where the polyp can be viewed.

More importantly, the dual-lens design of the egg-shaped image-capturing module of the first embodiment of the invention is able to provide a full-angle viewing of the internal structure of the colon without any blind spot. As such, it is possible to view the back side of the fold. FIGS. 7A and 7B show a use of the egg-shaped image-capturing module. In FIG. 7A, when the egg-shaped image-capturing module propels to a position in the colon 30, a polyp 40 may be located at a back side of the fold where the first image detector D1 is not able to view. However, as the egg-shaped image-capturing module reaches another position as shown in FIG. 7B, the second image detector D2 is able to view the polyp 40 which the first image detector D1 was unable to view.

In the invention, the egg-shaped image-capturing module is propelled by the vibration force. The use of the vibration force as a power source can reduce the uncomfortable feeling of the patient. Thus, the propelling method of the image-capturing module is critical to achieving the desired advantage of the invention. There are three approaches to drive the egg-shaped image-capturing module of the first embodiment of the invention. In the first approach, the egg-shaped image-capturing module can propel under the gravitational force and the vibration force. In the second approach, the egg-shaped image-capturing module can propel under the magnetic force and the vibration force. In the third approach, the egg-shaped image-capturing module can propel under the gravitational force, the magnetic force and the vibration force altogether.

Figure 8A:
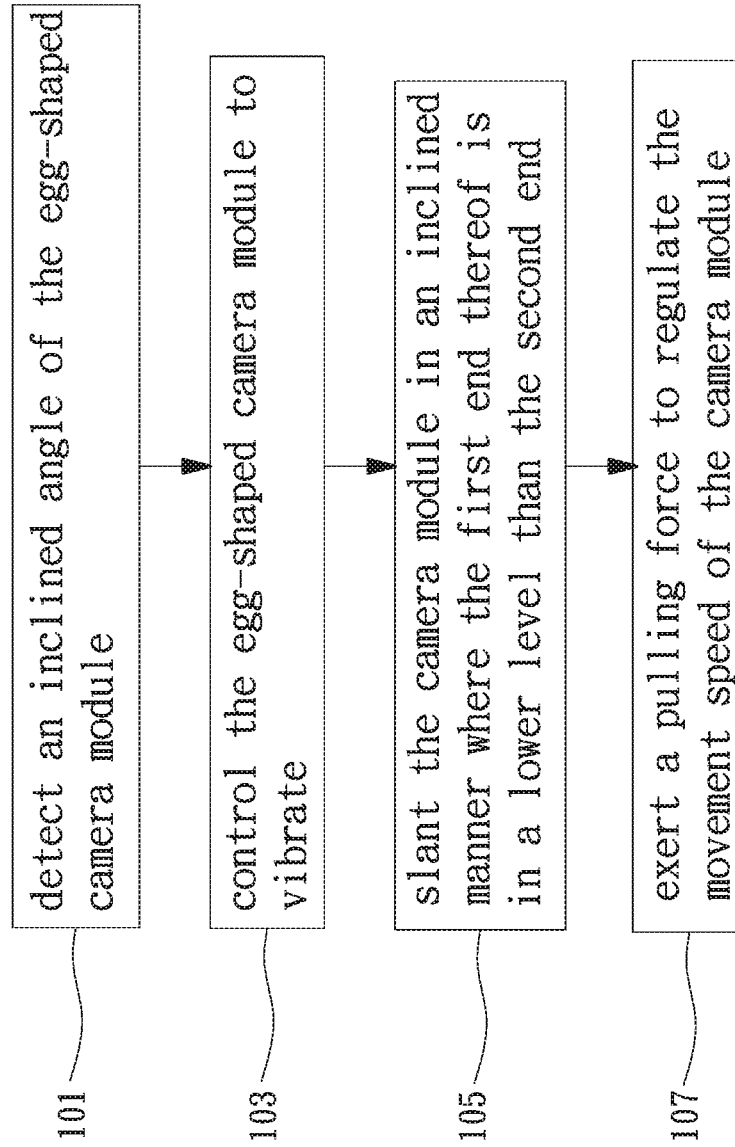
FIG. 8A shows a flowchart of a propelling method of the egg-shaped image-capturing module according to a second embodiment of the invention.

FIG. 8A shows a flowchart of a propelling method of the egg-shaped image-capturing module according to a second embodiment of the invention, which includes steps 101, 103 and 105, as elaborated below.

In the step 101, an inclined angle of the egg-shaped image-capturing module is detected. In the step 103, the egg-shaped image-capturing module is controlled to vibrate. In the step 105, during the vibration, the egg-shaped image-capturing module is slanted in an inclined manner where the first end 11a thereof is in a lower level than the second end 11b. The egg-shaped image-capturing module can be slanted by deviating the intestinal tract from the horizontal line. In this case, the egg-shaped image-capturing module is heading downwards. Specifically, since the inclined angle of the intestinal tract is detected and the inner condition of the intestinal tract is observed by the first image detector D1, there are many ways to adjust the inclined angle of the intestinal tract if the egg-shaped image-capturing module is not in the desired inclined state (with the first end 11a not heading downwards). In one of the approaches, the doctor can adjust the lying gesture of the patient to slant the intestinal tract in a desired inclined manner. In another approach, the doctor can incline the sickbed to slant the intestinal tract of the patient in a desired inclination. More specifically, when the egg-shaped image-capturing module reaches the descending colon, the doctor can incline the sickbed to lift the head of the patient and to lower the legs of the patient. In this situation, the egg-shaped image-capturing module can be in an inclined state where the first end 11a thereof is heading downwards. Then, based on the inclined angle of the intestinal tract, the doctor can adjust the local position of the intestinal tract in order to slant the egg-shaped image-capturing module in the desired inclined state. As such, the first end 11a of the egg-shaped image-capturing module can be heading downwards, allowing the image-capturing module to propel along the descending colon more easily. As another example, when the egg-shaped image-capturing module reaches the bend between the descending colon and the transverse colon, the patient can be in the right side lying position to allow the image-capturing module to propel more easily in the transverse colon. Alternatively, the doctor can squeeze a part of the intestinal tract to allow the egg-shaped image-capturing module to propel more smoothly. In addition to the steps 101, 103 and 105, the propelling method of the egg-shaped image-capturing module according to the second embodiment of the invention may further include a step 107. In the step 107, a pulling force is exerted to regulate the propelling speed of the egg-shaped image-capturing module and to adjust the propelling direction of the image-capturing module. The step 107 is provided to slow down the egg-shaped image-capturing module when the image-capturing module propels too fast, as well as to adjust the direction of the image-capturing module when the image-capturing module deviates from the desired propelling direction and gets stuck in the intestinal tract. The pulling force is exerted by pulling the wiring unit 20.

Figure 8B:
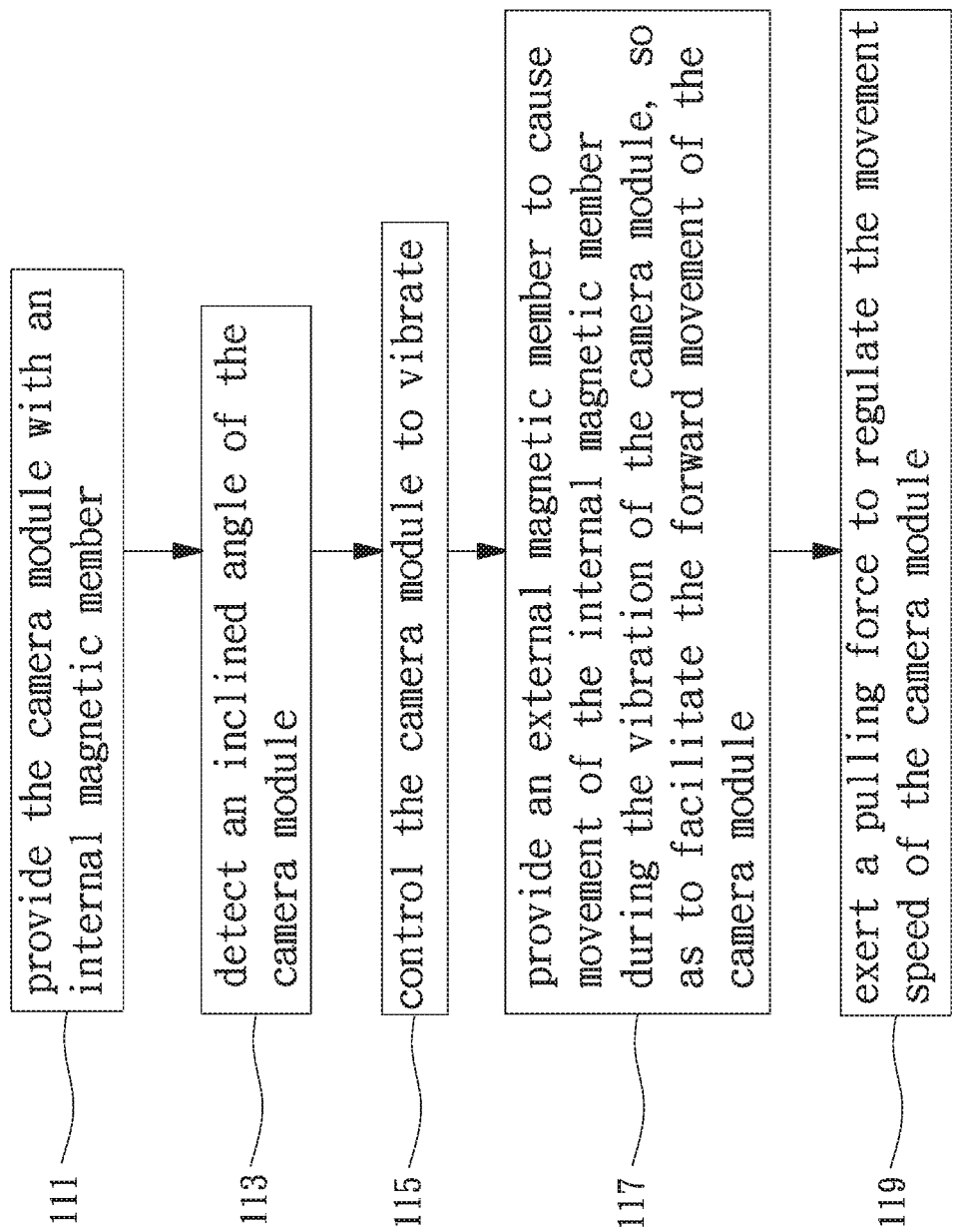
FIG. 8B shows a flowchart of a propelling method of the egg-shaped image-capturing module according to a third embodiment of the invention.

FIG. 8B shows a flowchart of a propelling method of the egg-shaped image-capturing module according to a third embodiment of the invention. The propelling method in the third embodiment uses the magnetic force as a power source of the egg-shaped image-capturing module. Namely, the propelling method uses the magnetic force to control the propelling of the egg-shaped image-capturing module shown in FIG. 4A. The flowchart includes steps 111, 113, 115 and 117, as elaborated below.

In the step 111, an internal magnetic member is provided. In the step 113, an inclined angle of the egg-shaped image-capturing module is detected. In the step 115, the egg-shaped image-capturing module is controlled to vibrate. In the step 117, an external magnetic member is provided to propel the internal magnetic member during the vibration, so as to facilitate propelling the egg-shaped image-capturing module. Since the inclined angle of the egg-shaped image-capturing module is detected, the external magnetic member can be used to propel the image-capturing module during the movement thereof. This can be observed from the image captured by the first image detector D1. Thus, during the vibration of the egg-shaped image-capturing module, the external magnetic member can provide a small auxiliary momentum to facilitate propelling the image-capturing module.

Similarly, in addition to the steps 111, 113, 115 and 117, the propelling method of the egg-shaped image-capturing module according to the third embodiment of the invention may further include a step 119. In the step 119, a pulling force is exerted to regulate the propelling speed of the egg-shaped image-capturing module and to adjust the propelling direction of the image-capturing module. The step 119 is not elaborated herein as it is similar to the step 107 previously discussed.

Figure 9A:
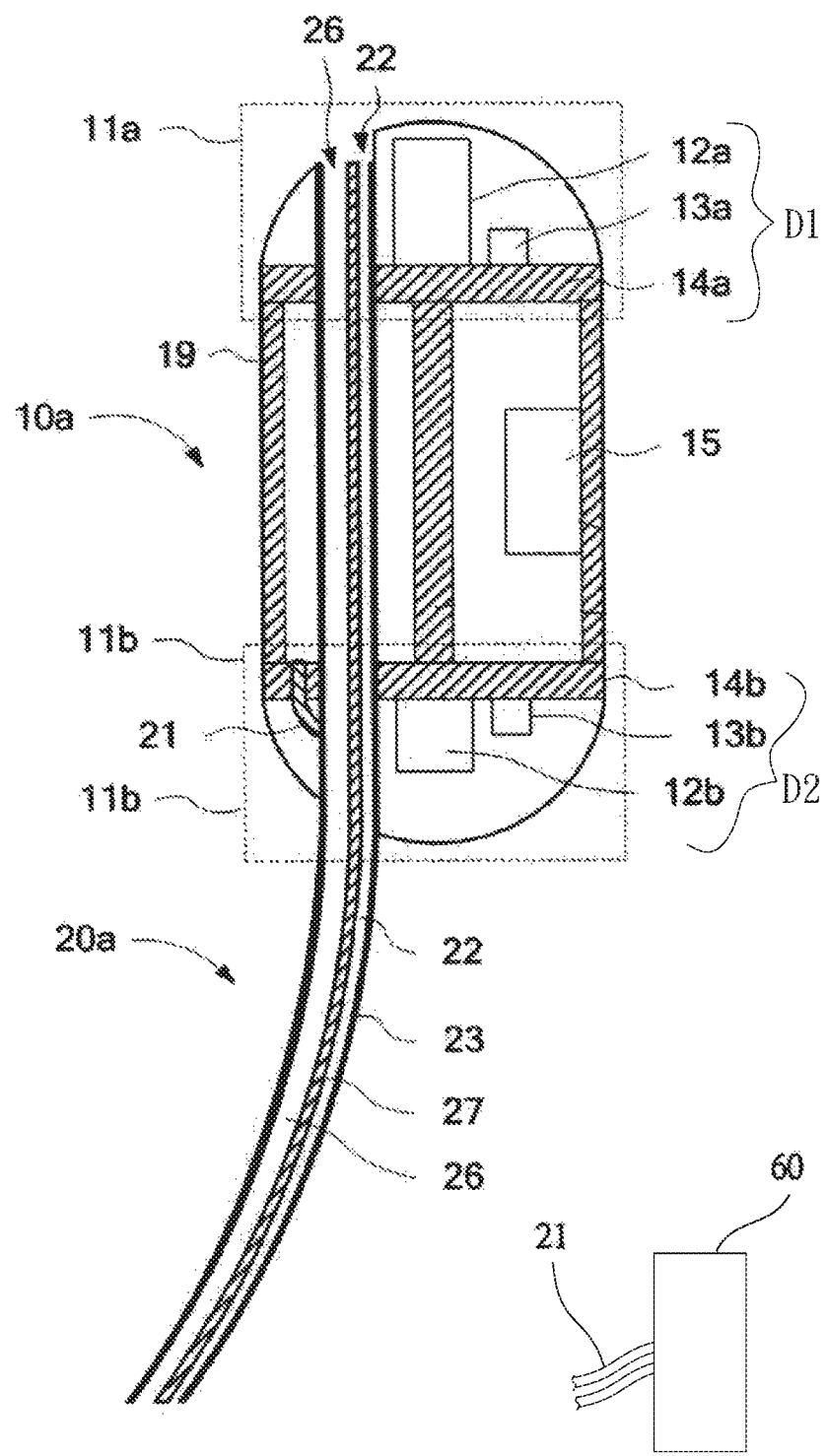
FIG. 9A is a cross sectional view of an egg-shaped image-capturing module of a colonoscope according to a fourth embodiment of the invention.
Figure 9B:
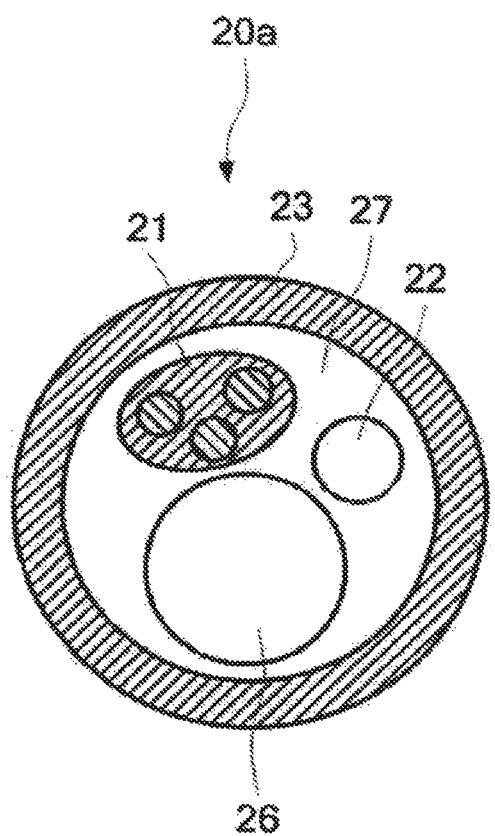
FIG. 9B is a cross sectional view of an exposed part of a wiring unit of the image-capturing module shown in FIG. 9A.
Figure 9C:
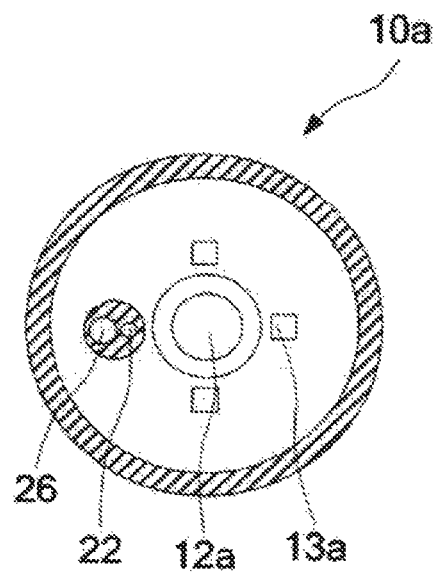
FIG. 9C is a radially cross sectional view of the first end of the casing shown in FIG. 9A.
Figure 10:
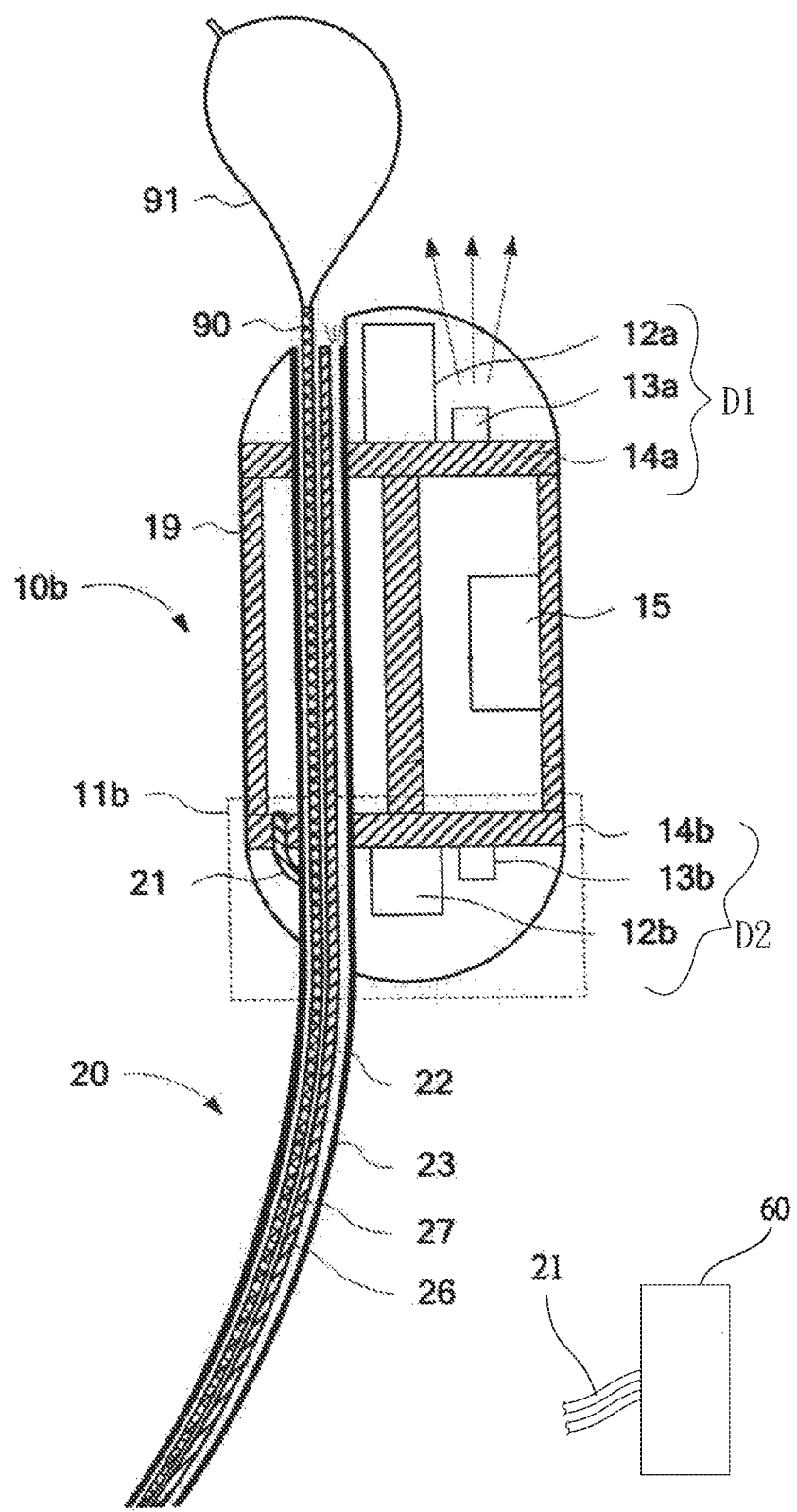
FIG. 10 is a cross sectional view of the egg-shaped image-capturing module of FIG. 9A where a polypectomy snare is used in the surgery.

FIG. 9A is a cross sectional view of an egg-shaped image-capturing module of a colonoscope according to a fourth embodiment of the invention. FIG. 9B is a cross sectional view of an exposed part of a wiring unit of the image-capturing module shown in FIG. 9A. FIG. 9C is a cross sectional view of the first end 11a of the casing 10 shown in FIG. 9A. In the fourth embodiment, the wiring unit 20a further includes an instrument channel 26 in addition to the air tube 22. The air tube 22 and the instrument channel 26 lead to the same outlet at the first end 11a of the casing 10. In the fourth embodiment, the outlet is arranged near the first image capturing device 12a, such that a polypectomy snare 90 (as shown in FIG. 10), a hemostatic needle, a biopsy forcep or a foreign body forcep can be extended into the instrument channel 26 to perform the related surgery. The egg-shaped image-capturing module of the colonoscope according to the fourth embodiment of the invention can also include the internal and external magnetic members as shown in FIGS. 4A and 4B. As such, the internal and external magnetic members can be magnetically attracted to each other under the magnetic force during the surgery, such that the doctor is able to perform the related surgery on the affected part.

In the cross sectional view of the wiring unit 20a as shown in FIG. 9B, the wiring unit 20a further includes the instrument channel 26 and a filling 27 in addition to the plurality of lead wires 21 (including the positive power line, the negative power line, the signal line and the outer sheath 23) and the air tube 22. The filling 27 can provide a reinforced effect for the wiring unit 20a. In FIG. 9A, the outlet at the first end 11a does not include the plurality of lead wires 21. Instead, the plurality of lead wires 21 extends out of the outer sheath 23 at the second end 11b and is welded to the second circuit board 14b. This forms a special type of the wiring unit 20a. However, the plurality of lead wires 21 may also extend out of the outer sheath 23 at the first end 11a and is welded to the first circuit board 14a (this is not shown).

In FIG. 9C, the air tube 22 and the instrument channel 26 are next to the first image capturing device 12a. As such, when an instrument extends out of the instrument channel 26, the doctor can clearly see the instrument and accurately perform the surgery as shown in FIG. 10.

FIG. 10 is a cross sectional view of the egg-shaped image-capturing module of FIG. 9A where the polypectomy snare 90 extends through the image-capturing module in order to perform the surgery. In this arrangement, air can be pumped into the intestinal tract through the air tube 22 to expand the colon, and liquid can be sprayed into the intestinal tract through the air tube 22 to lubricate the intestinal tract. The first light emitting unit 13a can be controlled to generate the light with different colors. As such, a respective color of the light can be irradiated into the intestinal tract, and the first image capturing device 12a can capture the images under the illumination of the light. Alternatively, the first image capturing device 12a can be replaced by a lens with adjustable zoom ratio such that the first image capturing device 12a can capture the image in a low or high zoom ratio. The first image capturing device 12a can capture the image of the cells in a high zoom ratio to provide a more accurate diagnosis.

In FIG. 9A, the arrangement of the instrument channel 26 allows different types of instruments to reach the first end 11a of the egg-shaped image-capturing module. In this regard, the polypectomy snare 90 extends into the instrument channel 26. The polypectomy snare 90 can also extend out of the instrument channel 26 to excise the polyp.

Figure 11A:
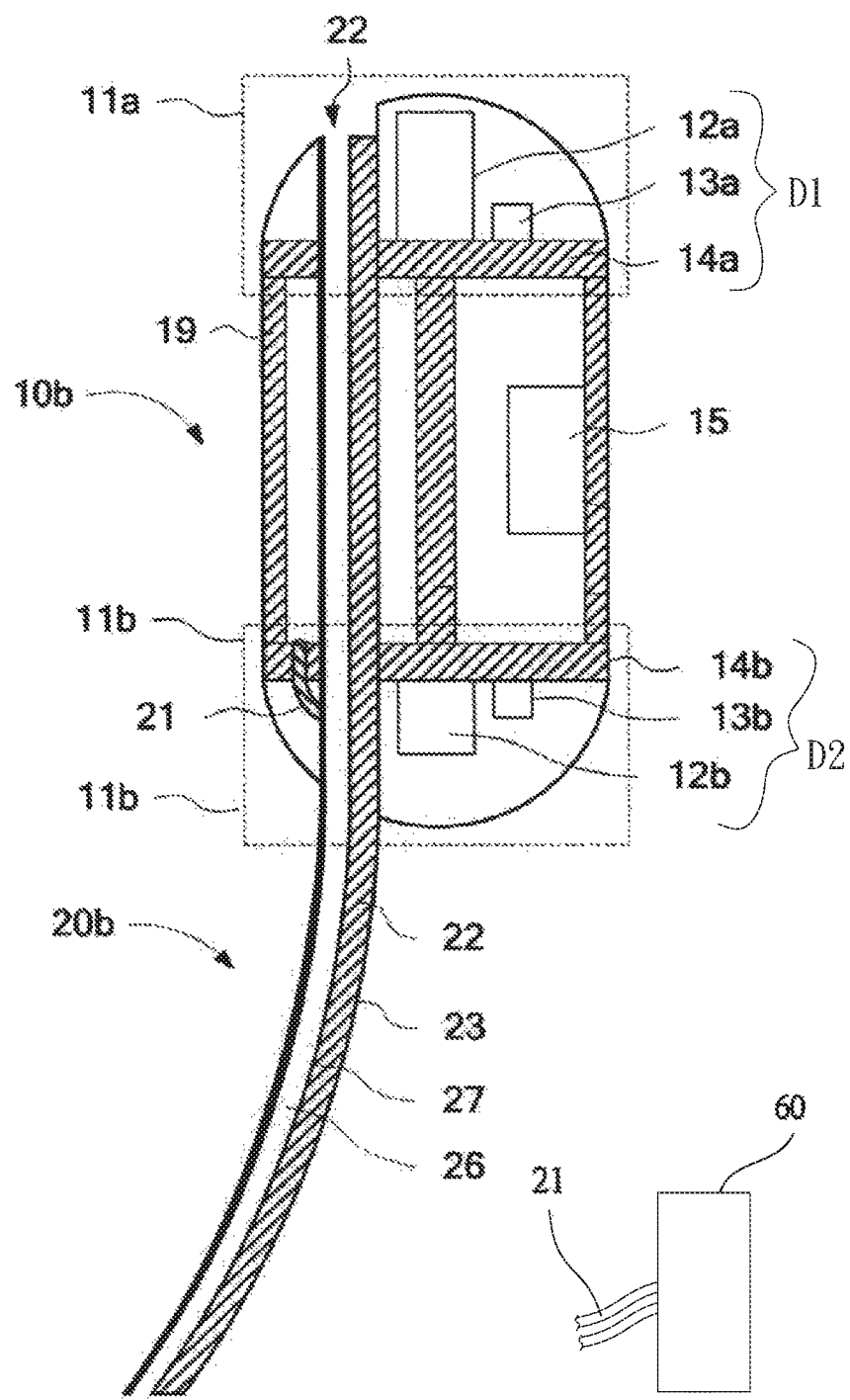
FIG. 11A is a cross sectional view of an egg-shaped image-capturing module of a colonoscope according to a fifth embodiment of the invention.
Figure 11B:
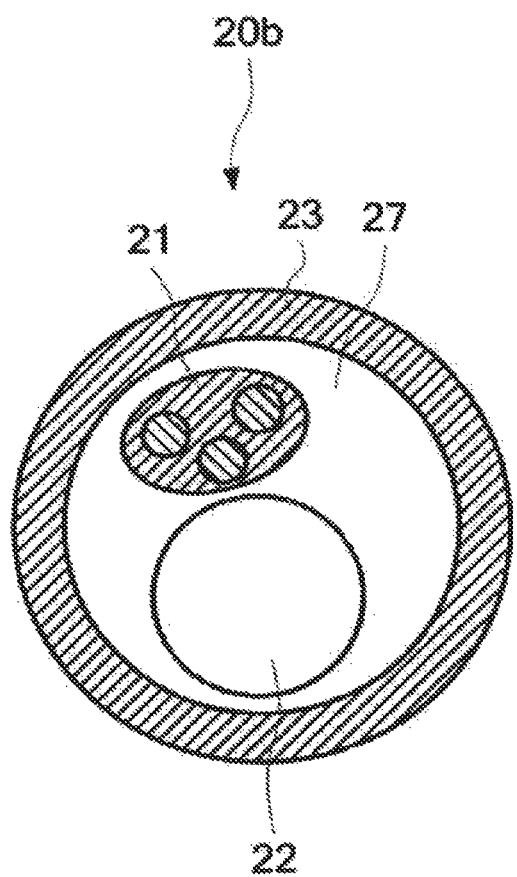
FIG. 11B is a cross sectional view of an exposed part of a wiring unit of the image-capturing module of FIG. 11A.
Figure 11C:
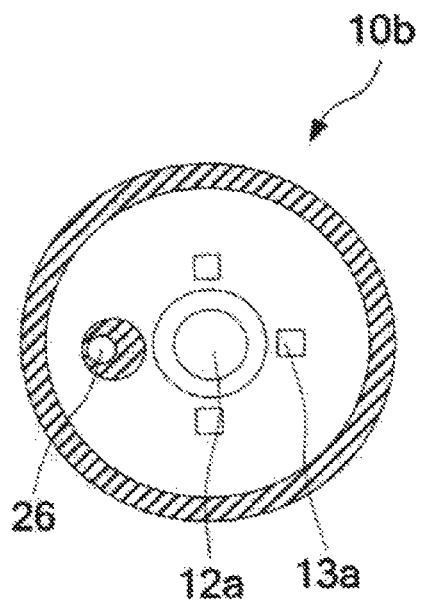
FIG. 11C is a cross sectional view of the first end of the image-capturing module of FIG. 11A.
Figure 12:
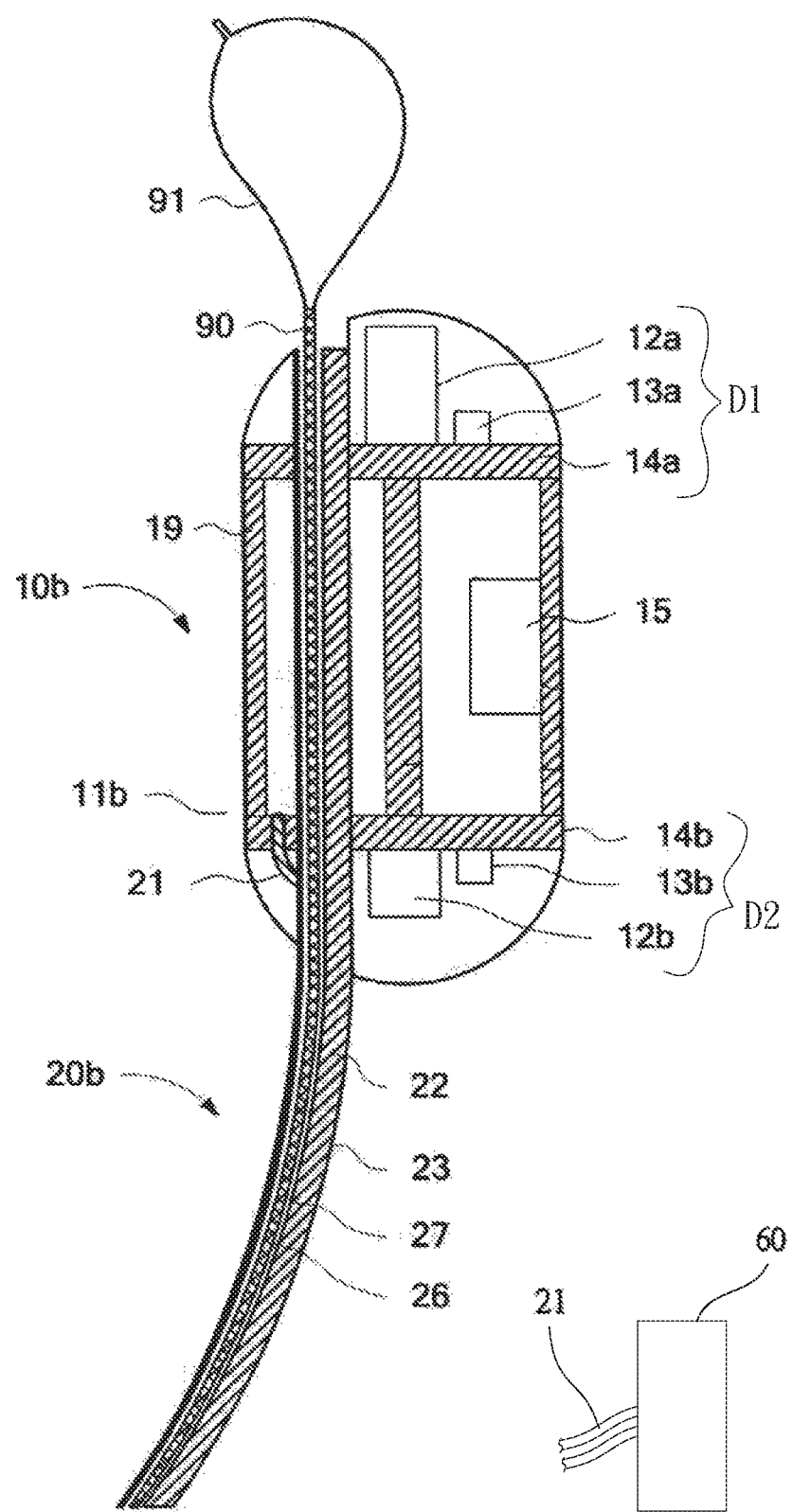
FIG. 12 is a cross sectional view of the egg-shaped image-capturing module of FIG. 11A where a polypectomy snare is used in the surgery.

FIGS. 11A, 11B and 11C show an egg-shaped image-capturing module of a colonoscope according to a fifth embodiment of the invention. In FIG. 11A, a cross sectional view of the egg-shaped image-capturing module is shown. In FIG. 11B, a cross sectional view of an exposed part of a wiring unit of the image-capturing module is shown. In FIG. 11C, a cross sectional view of the first end 11a of the image-capturing module is shown. FIG. 12 is a cross sectional view of the egg-shaped image-capturing module of FIGS. 11A-11C when the image-capturing module is used in a surgery. In comparison with the fourth embodiment, the wiring unit 20a in the fifth embodiment does not include the instrument channel 26. Instead, the air tube 22 is used to replace the instrument channel. Thus, the air tube 22 allows the passage of air, liquid and an instrument.

Figure 13A:
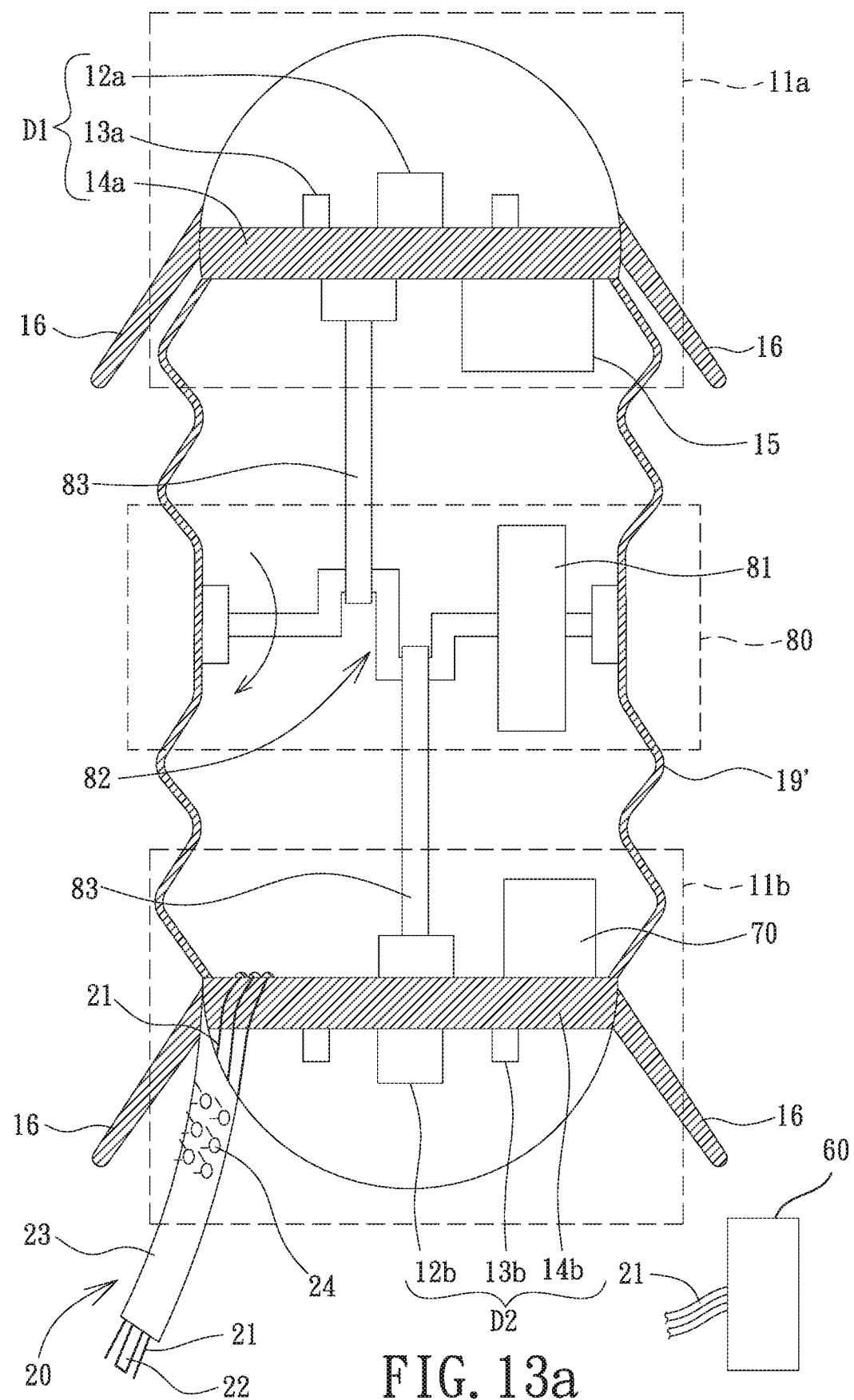
FIG. 13A is a cross sectional view of an egg-shaped image-capturing module of a colonoscope according to a sixth embodiment of the invention where the casing of the image-capturing module is in a fully-stretched state.
Figure 13B:
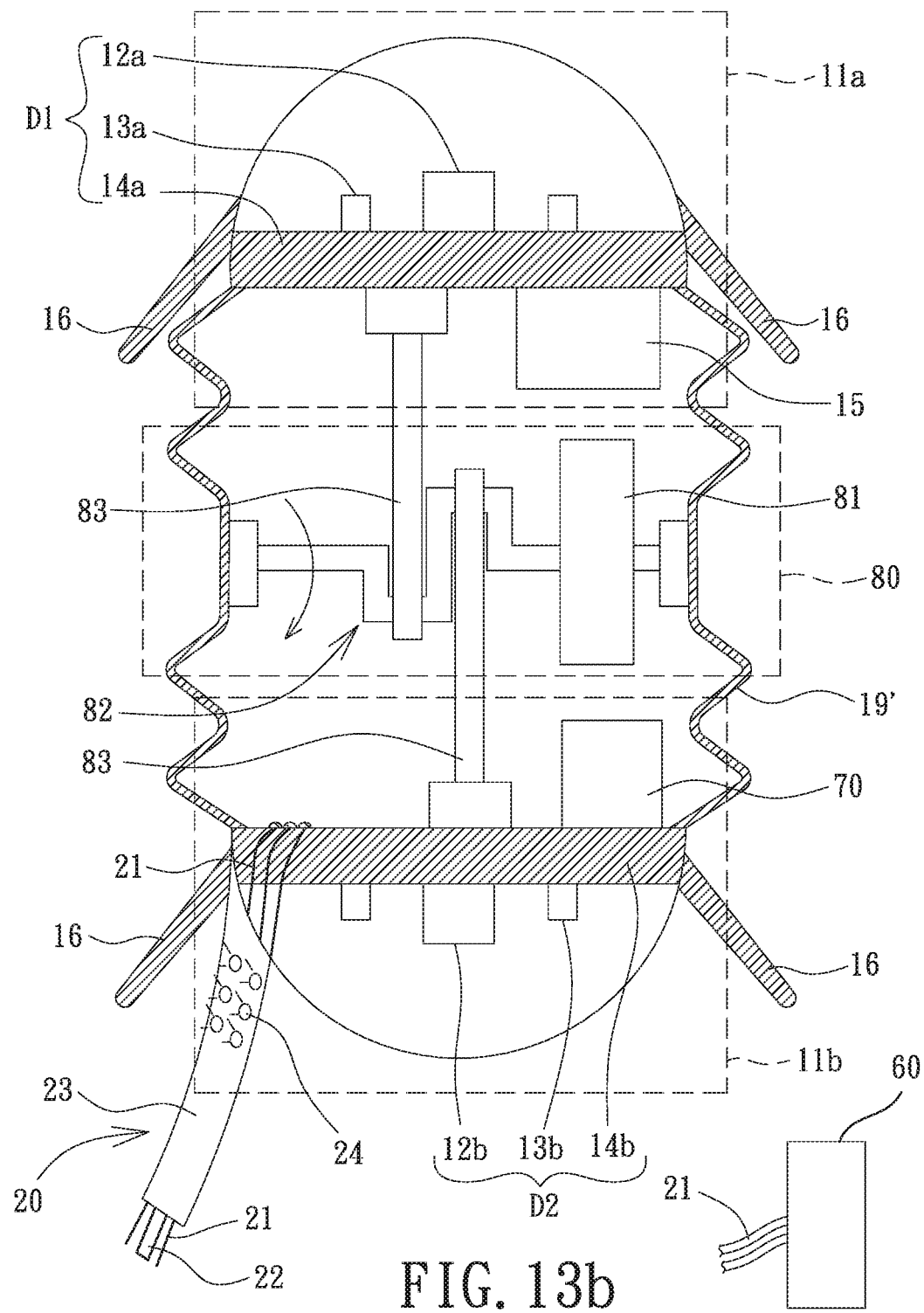
FIG. 13B is a cross sectional view of the egg-shaped image-capturing module of FIG. 13A where the casing of the image-capturing module is in a fully-retracted state.
Figure 13C:
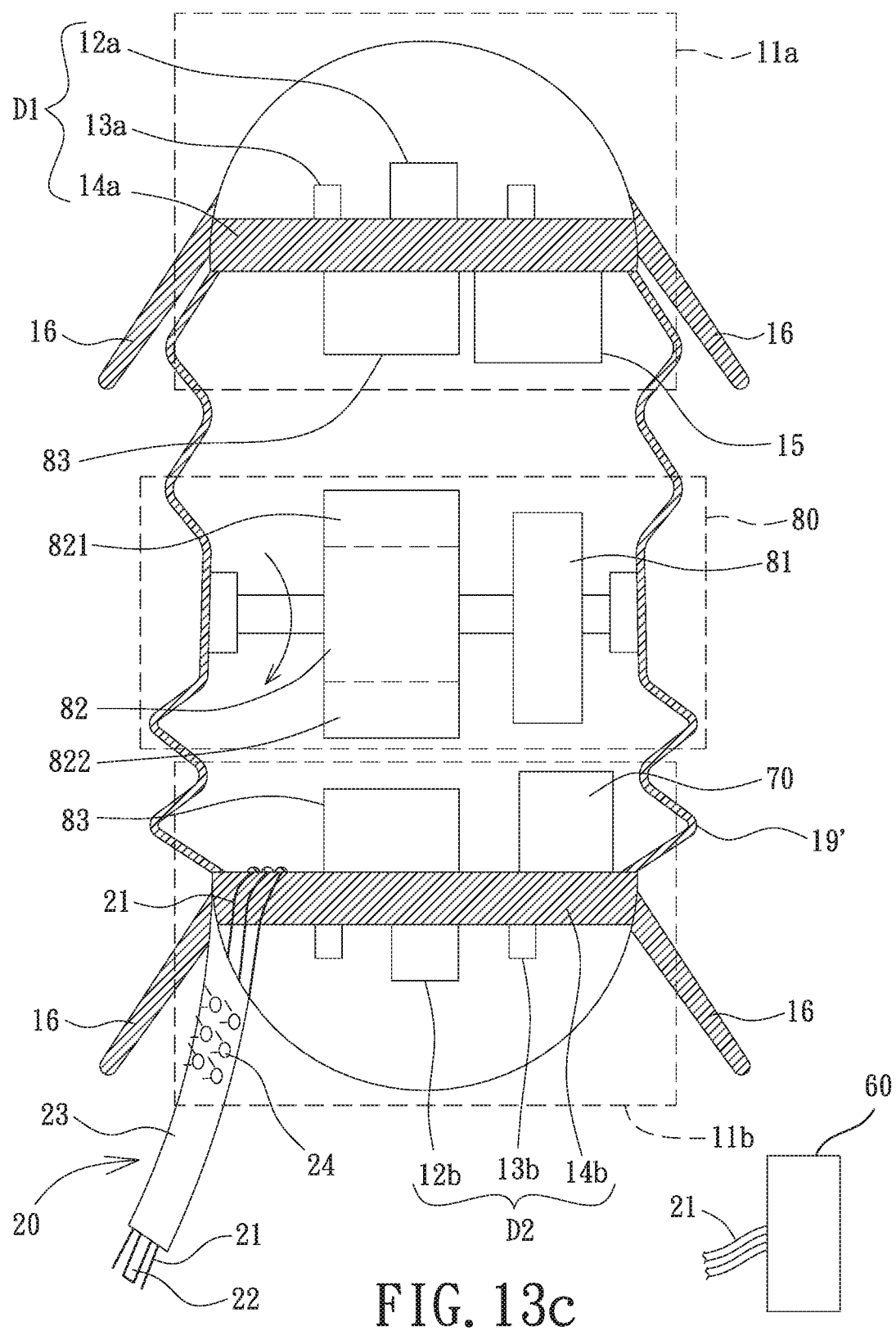
FIG. 13C is a cross sectional view of the egg-shaped image-capturing module of FIG. 13A where the casing of the image-capturing module is partially stretched.

FIGS. 13A, 13B and 13C are cross sectional views of an egg-shaped image-capturing module of a colonoscope according to a sixth embodiment of the invention. The egg-shaped image-capturing module in this embodiment differs from that in the first embodiment in that the lateral wall 19' of the egg-shaped casing 10c is made of a flexible material. The vibration motor 15 and the angle detection unit 70 are mounted on the first circuit board 14a or the second circuit board 14b. In addition, the first circuit board 14a and the second circuit board 14b are electrically connected to each other via a flexible lead wire. The egg-shaped image-capturing module in the sixth embodiment is characterized in that the casing 10c includes a telescopic propelling control unit 80 connected between the first end 11a and the second end 11b of the casing 10c. Also, the casing 10c includes the propelling auxiliaries 16 on an outer surface thereof. Specifically, the telescopic propelling control unit 80 may be a structure that allows telescopic movement between the first end 11a and the second end 11b. The telescopic propelling control unit 80 includes a drive motor 81, a telescopically driving member 82 and a telescopically driven member 83. The drive motor 81 can be controlled by the control unit 60 and is preferably mounted to an inner side of the lateral wall 19'. The telescopically driving member 82 is rotatably coupled with the drive motor 81. The telescopically driven member 83 is mounted to the first circuit board 14a (which is at the first end 11a) and the second circuit board 14b (which is at the second end 11b). In another approach, the drive motor 81 is mounted to one of the first and second circuit boards 14a and 14b while the telescopically driven member 83 is mounted to another of the first and second circuit boards 14a and 14b. In this arrangement, when the drive motor 81 drives the telescopically driving member 82, the telescopically driven member 83 will move away from the telescopically driving member 82 (as shown in FIG. 13A) or towards the telescopically driving member 82 (as shown in FIG. 13B). As a result, the telescopic movement of the lateral wall 19' is attained. Under the telescopic movement of the lateral wall 19', the egg-shaped image-capturing module can smoothly pass through the narrow area or bending area of the intestinal tract. The egg-shaped image-capturing module can also propel under only the telescopic momentum.

More specifically, the telescopic propelling control unit 80 can include any structure that allows continuous telescopic movement between the first end 11a and the second end 11b of the casing 10c. As shown in FIGS. 13A and 13B, the telescopically driving member 82 is in the form of a crankshaft, and the telescopically driven member 83 is in the form of two interconnected rods. One of the rods is connected to the first circuit board 14a, and the other one is connected to the second circuit board 14b. In another option as shown in FIG. 13C, the telescopically driving member 82 is in the form of a rotor having a first magnetic pole face 821 and a second magnetic pole face 822. The first and second magnetic pole faces have opposite magnetic poles and are arranged on an outer face of the rotor. In this regard, the telescopically driven member 83 can be in the form of two magnets facing the telescopically driving member 82. In this arrangement, the first magnetic pole face 821 may be N pole, the second magnetic pole face 822 may be S pole, the upper magnet 83 may be S pole, and the lower magnet 83 may be N pole. As such, the telescopic movement of the lateral wall 19' may be attained based on the magnetically attractive and repulsive forces between the telescopically driving member 82 and the telescopically driven member 83. However, the rotor includes a plurality of first magnetic pole faces and a plurality of second magnetic pole faces that have opposite magnetic poles and are arranged on the outer face of the rotor in an alternating manner.

According to the structure of the egg-shaped image-capturing module of the sixth embodiment, its propelling method can also control the image-capturing module to propel telescopically after the inclined angle of the image-capturing module is detected. In this regard, the propelling method can slant the image-capturing module in an inclined state where the first end 11a thereof is in a lower level than the second end 11b. Based on the inclined state of the image-capturing module, the image-capturing module can propel under the telescopic momentum. Alternatively, the image-capturing module can also propel under the vibration force or the magnetic force (as mentioned previously) in addition to the telescopic force. Furthermore, since the casing 10c is provided with the propelling auxiliaries 16, the propelling auxiliaries 16 can abut the intestinal wall during the telescopic movement of the image-capturing module. As such, the propelling of the image-capturing module is facilitated.

The image-capturing module of the invention can be used in a colonoscope to provide a colonoscopy which is nearly pain-free, has no blind spot, and prevents intestinal perforation. The medical technology is therefore improved.

Although the control unit 60 is shown as being outside the egg-shaped casing 10 in the above embodiments, the control unit 60 can also be mounted in the egg-shaped casing 10 if the wireless transmission mechanism is used and a battery is contained in the egg-shaped casing 10.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A colonoscope comprising:
an image-capturing module comprising:
a casing having a first end and a second end, wherein the first and second ends are spaced from each other in an axial direction of the casing, and wherein the first end is made of a transparent material;
a first image detector arranged at the first end of the casing to provide an illumination effect and to capture a first image in a first direction; and
a vibration motor arranged in the casing and configured to vibrate the casing;
a control unit electrically connected to the first image detector and the vibration motor, wherein the control unit controls the first image detector to capture the first image and controls the transmission of the captured first image upon the reception of a command, and wherein the control unit controls the vibration of the vibration motor; and
a wiring unit fixed to the second end of the casing and comprising an outer sheath and an air tube, wherein the air tube is made of a flexible material and is enveloped in the outer sheath, wherein the wiring unit includes a power supply member electrically connected to the control unit and providing power to the first image detector and the vibration motor,
wherein the casing or the wiring unit includes a vent which is in communication with the air tube of the wiring unit, wherein the air tube is configured to convey an air, and wherein the vent is configured to output the conveyed air to a colon.

2. The colonoscope as claimed in claim 1, further comprising a second image detector arranged at the second end of the casing, wherein the second image detector is configured to capture a second image in a second direction substantially opposite to the first direction.

3. The colonoscope as claimed in claim 1, further comprising an angle detection unit electrically connected to the control unit, wherein the angle detection unit is configured to detect an inclined angle of the casing with respect to a horizontal line, and wherein the control unit transmits a detected result of the inclined angle to a display.

4. The colonoscope as claimed in claim 3, wherein the angle detection unit is a microelectromechanical angle detection chip, a microelectromechanical gyroscope chip, a microelectromechanical dual-axis acceleration detection chip, a microelectromechanical tri-axis acceleration detection chip, a rolling switch or a magnetic sensor.

5. The colonoscope as claimed in claim 1, further comprising at least one propelling auxiliary arranged on an outer surface of the casing, wherein the at least one propelling auxiliary is configured to facilitate propelling the image-capturing module.

6. The colonoscope as claimed in claim 1, wherein the power supply member is in a form of a plurality of lead wires contained in the wiring unit.

7. The colonoscope as claimed in claim 1, wherein the casing has a length of 2.5-5.2 cm and a width of 1.5-2.5 cm.

8. The colonoscope as claimed in claim 1, wherein the wiring unit or the air tube further comprises an instrument channel provided for insertion of an instrument, wherein the instrument channel has an outlet at the first end of the casing, and wherein the instrument is configured to extend into the instrument channel and extend out of the outlet for performing a surgery.

9. The colonoscope as claimed in claim 1, further comprising a telescopic propelling control unit connected between the first end and the second end of the casing, wherein the casing has a lateral wall made of a flexible material.

10. The colonoscope as claimed in claim 9, wherein the casing comprises at least one propelling auxiliary on an outer surface thereof.

11. The colonoscope as claimed in claim 9, wherein the telescopic propelling control unit comprises a drive motor, a telescopically driving member and a telescopically driven member, wherein the drive motor is mounted to an inner side of the lateral wall, wherein the telescopically driving member is rotatably coupled with the drive motor, and wherein the telescopically driven member is mounted to at least one of the first and second ends.

* * * * *